(12) United States Patent
Flynn et al.

(10) Patent No.: US 7,392,095 B2
(45) Date of Patent: Jun. 24, 2008

(54) EXTENDABLE AND RETRACTABLE LEAD HAVING A SNAP-FIT TERMINAL CONNECTOR

(75) Inventors: David M. Flynn, Lino Lakes, MN (US); Michael Brenzel, St. Paul, MN (US); Jason Skubitz, Minneapolis, MN (US); Larry L. Hum, Cottage Grove, MN (US); Carol Werlein, Ham Lake, MN (US); Christopher Paul Knapp, Oakdale, MN (US); Gregory R. Ley, New Brighton, MN (US); Jason Alan Shiroff, Las Vegas, NV (US); Brian David Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/173,664

(22) Filed: Jul. 1, 2005

(65) Prior Publication Data

US 2005/0267557 A1    Dec. 1, 2005

Related U.S. Application Data

(60) Continuation of application No. 10/264,494, filed on Oct. 4, 2002, now Pat. No. 6,915,169, which is a division of application No. 09/359,580, filed on Jul. 22, 1999, now Pat. No. 6,463,334, which is a continuation-in-part of application No. 09/121,005, filed on Jul. 22, 1998, now Pat. No. 6,141,594, and a continuation-in-part of application No. 09/120,824, filed on Jul. 22, 1998, now Pat. No. 6,212,434, and a continuation-in-part of application No. 09/184,226, filed on Nov. 2, 1998, now abandoned.

(51) Int. Cl.
*A61N 1/05* (2006.01)

(52) U.S. Cl. .................. 607/127; 607/116; 607/122
(58) Field of Classification Search ................ 607/2, 607/36–38, 115–116, 119, 122–123, 12; 600/372–375, 381
See application file for complete search history.

(56) References Cited

U.S. PATENT DOCUMENTS 3,569,852 A    3/1971    Berkovits (Continued)

FOREIGN PATENT DOCUMENTS

DE            133401           1/1979

(Continued)

OTHER PUBLICATIONS

"Coating Process for Composite Implants", *Medical Materials Update*, vol. 1, No. 12, (Jan. 1995), pp. 1 and 4.

(Continued)

*Primary Examiner*—Carl Layno
*Assistant Examiner*—Jon-Eric Morales
(74) *Attorney, Agent, or Firm*—Schwegman, Lundberg & Woessner, P.A.

(57) ABSTRACT

A lead having an extendable and retractable fixation mechanism has a rotating terminal pin at the terminal end which rotates the fixation mechanism at the distal end. As the terminal pin is rotated, the fixation mechanism is extended or retracted from the distal end of the lead. A threaded collar allows for the fixation mechanism to smoothly extend and retract from the lead, and allows for a 1:1 turn ratio between the terminal pin and the fixation mechanism. A fluoroscopic ring disposed at the distal end of the lead provides information during the implantation process.

20 Claims, 19 Drawing Sheets

U.S. PATENT DOCUMENTS

| | | |
|---|---|---|
| 3,590,811 A | 7/1971 | Harris |
| 3,614,955 A | 10/1971 | Mirowski |
| 3,656,487 A | 4/1972 | Gobeli |
| 3,804,098 A | 4/1974 | Friedman |
| 3,835,845 A | 9/1974 | Maher |
| 3,866,615 A | 2/1975 | Hewson |
| 3,878,833 A | 4/1975 | Arneson et al. |
| 3,911,928 A | 10/1975 | Lagergren |
| 3,926,197 A | 12/1975 | Alley, III |
| 3,927,677 A | 12/1975 | Gobeli et al. |
| 3,937,226 A | 2/1976 | Funke |
| 3,939,824 A | 2/1976 | Arneson et al. |
| 3,942,536 A | 3/1976 | Mirowski et al. |
| 3,949,757 A | 4/1976 | Sabel |
| 3,983,880 A | 10/1976 | Kolenik |
| 3,986,496 A | 10/1976 | Brastad |
| 3,999,556 A | 12/1976 | Alferness |
| 4,000,461 A | 12/1976 | Barber et al. |
| 4,010,758 A | 3/1977 | Rockland et al. |
| 4,013,081 A | 3/1977 | Kolenik |
| 4,026,303 A | 5/1977 | Babotai |
| 4,030,508 A | 6/1977 | Thalen |
| 4,030,509 A | 6/1977 | Heilman et al. |
| 4,033,355 A | 7/1977 | Amundson |
| 4,038,703 A | 8/1977 | Bokros |
| 4,057,067 A | 11/1977 | Lajos |
| 4,059,116 A | 11/1977 | Adams |
| 4,082,087 A | 4/1978 | Howson |
| 4,097,766 A | 6/1978 | Renirie |
| 4,106,512 A | 8/1978 | Bisping |
| 4,136,703 A | 1/1979 | Wittkampf |
| 4,146,037 A | 3/1979 | Flynn et al. |
| 4,154,247 A | 5/1979 | O'Neill |
| 4,156,429 A | 5/1979 | Amundson |
| 4,164,943 A | 8/1979 | Hill et al. |
| 4,170,999 A | 10/1979 | Allen et al. |
| 4,187,853 A | 2/1980 | Barton et al. |
| 4,202,340 A | 5/1980 | Langer et al. |
| 4,202,341 A | 5/1980 | Blaser |
| RE30,366 E | 8/1980 | Rasor et al. |
| 4,217,913 A | 8/1980 | Dutcher |
| 4,226,245 A | 10/1980 | Bennett, Jr. |
| 4,235,246 A | 11/1980 | Weiss |
| 4,240,442 A | 12/1980 | Andresen et al. |
| 4,250,883 A | 2/1981 | Thompson |
| 4,258,725 A | 3/1981 | O'Neill |
| 4,270,549 A | 6/1981 | Heilman |
| 4,278,093 A * | 7/1981 | Lafortune et al. ............. 607/37 |
| 4,282,885 A | 8/1981 | Bisping |
| 4,289,144 A | 9/1981 | Gilman |
| 4,291,707 A | 9/1981 | Heilman et al. |
| 4,299,239 A | 11/1981 | Weiss et al. |
| 4,311,133 A | 1/1982 | Robinson |
| 4,311,153 A | 1/1982 | Smits |
| 4,325,384 A | 4/1982 | Blaser et al. |
| 4,326,534 A | 4/1982 | Axelgaard et al. |
| 4,332,259 A | 6/1982 | McCorkle, Jr. |
| 4,363,325 A | 12/1982 | Roline et al. |
| 4,378,020 A | 3/1983 | Nappholz et al. |
| 4,393,883 A | 7/1983 | Smyth et al. |
| 4,402,329 A | 9/1983 | Williams |
| 4,407,288 A | 10/1983 | Langer et al. |
| 4,428,378 A | 1/1984 | Anderson et al. |
| 4,437,474 A | 3/1984 | Peers-Trevarton |
| 4,444,206 A | 4/1984 | Gold |
| 4,458,677 A | 7/1984 | McCorkle, Jr. |
| 4,458,695 A | 7/1984 | Peers-Trevarton |
| 4,463,765 A | 8/1984 | Gold |
| 4,469,104 A | 9/1984 | Peers-Trevarton |
| 4,485,813 A | 12/1984 | Anderson et al. |
| 4,497,326 A | 2/1985 | Curry |
| 4,498,478 A | 2/1985 | Bourgeois |
| 4,513,212 A | 4/1985 | Money |
| 4,523,593 A | 6/1985 | Rueter |
| 4,532,931 A | 8/1985 | Mills |
| 4,540,236 A | 9/1985 | Peers-Trevarton |
| 4,548,203 A | 10/1985 | Tacker, Jr. et al. |
| 4,549,548 A | 10/1985 | Wittkampf et al. |
| 4,553,548 A | 11/1985 | Varrichio et al. |
| 4,559,946 A | 12/1985 | Mower |
| 4,559,951 A | 12/1985 | Dahl et al. |
| 4,567,900 A | 2/1986 | Moore |
| 4,567,901 A | 2/1986 | Harris |
| 4,570,642 A | 2/1986 | Kane et al. |
| 4,577,643 A | 3/1986 | Beranek |
| 4,587,975 A | 5/1986 | Salo et al. |
| 4,595,009 A | 6/1986 | Leinders |
| 4,602,645 A | 7/1986 | Barrington et al. |
| 4,603,705 A | 8/1986 | Speicher et al. |
| 4,608,986 A | 9/1986 | Beranek et al. |
| 4,617,938 A | 10/1986 | Shimoni et al. |
| 4,624,265 A | 11/1986 | Grassi |
| 4,624,266 A | 11/1986 | Kane |
| 4,627,439 A | 12/1986 | Harris |
| 4,633,880 A | 1/1987 | Osypka et al. |
| 4,637,397 A | 1/1987 | Jones et al. |
| 4,641,656 A | 2/1987 | Smits |
| 4,643,201 A | 2/1987 | Stokes |
| 4,646,755 A | 3/1987 | Kane |
| 4,649,937 A | 3/1987 | DeHaan et al. |
| 4,649,938 A | 3/1987 | McArthur |
| 4,662,377 A | 5/1987 | Heilman et al. |
| 4,662,382 A | 5/1987 | Sluetz et al. |
| 4,664,113 A | 5/1987 | Frisbie et al. |
| 4,665,919 A | 5/1987 | Mensink et al. |
| 4,667,686 A | 5/1987 | Peers-Travarton |
| 4,677,986 A | 7/1987 | DeCote, Jr. |
| 4,679,572 A | 7/1987 | Baker, Jr. |
| 4,693,253 A | 9/1987 | Adams |
| 4,693,258 A | 9/1987 | Osypka et al. |
| 4,702,253 A | 10/1987 | Nappholz et al. |
| 4,708,144 A | 11/1987 | Hamilton et al. |
| 4,708,145 A | 11/1987 | Tacker, Jr. et al. |
| 4,721,115 A | 1/1988 | Owens |
| 4,722,351 A | 2/1988 | Phillipps et al. |
| 4,722,353 A | 2/1988 | Sluetz |
| 4,727,877 A | 3/1988 | Kallok |
| 4,741,342 A | 5/1988 | Stotts |
| 4,762,136 A | 8/1988 | Baker, Jr. |
| 4,763,646 A | 8/1988 | Lekholm |
| 4,766,902 A | 8/1988 | Schroeppel |
| 4,768,511 A | 9/1988 | DeCote, Jr. |
| 4,773,401 A | 9/1988 | Citak et al. |
| 4,774,952 A | 10/1988 | Smits |
| 4,775,950 A | 10/1988 | Terada et al. |
| 4,779,617 A | 10/1988 | Whigham |
| 4,782,836 A | 11/1988 | Alt |
| 4,784,161 A | 11/1988 | Skalsky et al. |
| 4,787,389 A | 11/1988 | Tarjan |
| 4,788,980 A | 12/1988 | Mann et al. |
| 4,799,486 A | 1/1989 | DuFault |
| 4,799,493 A | 1/1989 | DuFault |
| 4,800,883 A | 1/1989 | Winstrom |
| 4,817,608 A | 4/1989 | Shapland et al. |
| 4,817,634 A | 4/1989 | Holleman et al. |
| 4,819,643 A | 4/1989 | Menken |
| 4,819,647 A | 4/1989 | Byers et al. |
| 4,819,661 A | 4/1989 | Heil, Jr. et al. |
| 4,819,662 A | 4/1989 | Heil, Jr. et al. |
| 4,821,723 A | 4/1989 | Baker, Jr. et al. |
| 4,821,724 A | 4/1989 | Whigham et al. |
| 4,827,932 A | 5/1989 | Ideker et al. |
| 4,827,934 A | 5/1989 | Ekwall |
| 4,827,940 A | 5/1989 | Mayer et al. |

| Patent | Date | Inventor |
|---|---|---|
| 4,830,006 A | 5/1989 | Haluska et al. |
| 4,834,100 A | 5/1989 | Charms |
| 4,850,357 A | 7/1989 | Bach, Jr. |
| 4,858,623 A | 8/1989 | Bradshaw et al. |
| 4,860,750 A | 8/1989 | Frey et al. |
| 4,860,769 A | 8/1989 | Fogarty et al. |
| 4,865,037 A | 9/1989 | Chin et al. |
| 4,876,109 A | 10/1989 | Mayer et al. |
| 4,880,004 A | 11/1989 | Baker, Jr. et al. |
| 4,886,074 A | 12/1989 | Bisping |
| 4,903,699 A | 2/1990 | Baker, Jr. et al. |
| 4,903,700 A | 2/1990 | Whigham et al. |
| 4,905,691 A | 3/1990 | Rydell |
| 4,913,164 A | 4/1990 | Greene et al. |
| 4,919,135 A | 4/1990 | Phillips, Jr. et al. |
| 4,922,607 A | 5/1990 | Doan et al. |
| 4,922,927 A | 5/1990 | Fine et al. |
| 4,924,881 A | 5/1990 | Brewer |
| 4,932,969 A | 6/1990 | Frey et al. |
| 4,934,376 A | 6/1990 | Armington |
| 4,938,231 A | 7/1990 | Milijasevic et al. |
| 4,940,054 A | 7/1990 | Grevis et al. |
| 4,944,300 A | 7/1990 | Saksena |
| 4,949,719 A | 8/1990 | Pless et al. |
| 4,951,667 A | 8/1990 | Markowitz et al. |
| 4,951,668 A | 8/1990 | Reed |
| 4,953,551 A | 9/1990 | Mehra et al. |
| 4,953,564 A | 9/1990 | Berthelsen |
| 4,959,621 A | 9/1990 | Hosticka et al. |
| 4,962,767 A | 10/1990 | Brownlee |
| 4,966,146 A | 10/1990 | Webb et al. |
| 4,967,747 A | 11/1990 | Carroll et al. |
| 4,967,766 A | 11/1990 | Bradshaw |
| 4,969,463 A | 11/1990 | Dahl et al. |
| 4,971,070 A | 11/1990 | Holleman et al. |
| 4,972,835 A | 11/1990 | Carroll et al. |
| 4,972,848 A | 11/1990 | DiDomenico et al. |
| 4,984,572 A | 1/1991 | Cohen |
| 4,994,078 A | 2/1991 | Jarvik |
| 4,996,984 A | 3/1991 | Sweeney |
| 4,998,531 A | 3/1991 | Bocchi et al. |
| 4,998,975 A | 3/1991 | Cohen et al. |
| 5,000,177 A | 3/1991 | Hoffmann et al. |
| 5,002,067 A | 3/1991 | Berthelsen et al. |
| 5,003,990 A | 4/1991 | Osypka |
| 5,007,422 A | 4/1991 | Pless et al. |
| 5,007,864 A | 4/1991 | Stutz, Jr. |
| 5,010,887 A | 4/1991 | Thornander |
| 5,014,704 A | 5/1991 | Alt |
| 5,016,645 A | 5/1991 | Williams et al. |
| 5,016,646 A | 5/1991 | Gotthardt et al. |
| 5,016,808 A | 5/1991 | Heil, Jr. et al. |
| 5,018,523 A | 5/1991 | Bach, Jr. et al. |
| 5,020,544 A | 6/1991 | Dahl et al. |
| 5,024,221 A | 6/1991 | Morgan |
| 5,027,813 A | 7/1991 | Pederson et al. |
| 5,044,375 A | 9/1991 | Bach, Jr. et al. |
| 5,048,521 A | 9/1991 | Pless et al. |
| 5,050,001 A | 9/1991 | Kupersmith et al. |
| 5,050,599 A | 9/1991 | Hoegnelid |
| 5,050,601 A | 9/1991 | Kupersmith et al. |
| 5,052,407 A | 10/1991 | Hauser et al. |
| 5,056,516 A | 10/1991 | Spehr |
| 5,063,927 A | 11/1991 | Webb et al. |
| 5,063,932 A | 11/1991 | Dahl et al. |
| 5,065,766 A | 11/1991 | Sasaki |
| 5,070,605 A | 12/1991 | Daglow et al. |
| 5,074,313 A | 12/1991 | Dahl et al. |
| 5,076,272 A | 12/1991 | Ferek-Petric |
| 5,076,285 A | 12/1991 | Hess et al. |
| 5,083,562 A | 1/1992 | de Coriolis et al. |
| 5,085,213 A | 2/1992 | Cohen |
| 5,085,218 A | 2/1992 | Heil, Jr. et al. |
| 5,086,773 A | 2/1992 | Ware |
| 5,090,422 A | 2/1992 | Dahl et al. |
| 5,092,879 A | 3/1992 | Jarvik |
| 5,103,819 A | 4/1992 | Baker et al. |
| 5,105,826 A | 4/1992 | Smits et al. |
| 5,107,834 A | 4/1992 | Ideker et al. |
| 5,107,850 A | 4/1992 | Olive |
| 5,109,863 A | 5/1992 | Semmlow et al. |
| 5,111,811 A | 5/1992 | Smits |
| 5,111,812 A | 5/1992 | Swanson et al. |
| 5,111,816 A | 5/1992 | Pless et al. |
| 5,117,824 A | 6/1992 | Keimel et al. |
| 5,129,392 A | 7/1992 | Bardy et al. |
| 5,129,404 A | 7/1992 | Spehr et al. |
| 5,133,353 A | 7/1992 | Hauser |
| 5,133,365 A | 7/1992 | Heil, Jr. et al. |
| 5,137,019 A | 8/1992 | Pederson et al. |
| 5,139,033 A | 8/1992 | Everett et al. |
| 5,143,089 A | 9/1992 | Alt |
| 5,143,090 A | 9/1992 | Dutcher et al. |
| 5,144,949 A | 9/1992 | Olson |
| 5,144,960 A | 9/1992 | Mehra et al. |
| 5,152,299 A | 10/1992 | Soukup |
| 5,154,485 A | 10/1992 | Fleishman |
| 5,161,527 A | 11/1992 | Nappholz et al. |
| 5,161,528 A | 11/1992 | Sweeney |
| 5,163,428 A | 11/1992 | Pless |
| 5,165,403 A | 11/1992 | Mehra |
| 5,174,289 A | 12/1992 | Cohen |
| 5,174,303 A | 12/1992 | Schroeppel |
| 5,178,140 A | 1/1993 | Ibrahim |
| 5,178,154 A | 1/1993 | Ackmann et al. |
| 5,179,945 A | 1/1993 | Hofwegen et al. |
| 5,179,962 A | 1/1993 | Dutcher et al. |
| 5,181,511 A | 1/1993 | Nickolls et al. |
| 5,181,526 A | 1/1993 | Yamasaki |
| 5,188,105 A | 2/1993 | Keimel |
| 5,193,535 A | 3/1993 | Bardy et al. |
| 5,193,536 A | 3/1993 | Mehra |
| 5,199,429 A | 4/1993 | Kroll et al. |
| 5,203,348 A | 4/1993 | Dahl et al. |
| 5,205,283 A | 4/1993 | Olson |
| 5,209,229 A | 5/1993 | Gilli |
| 5,215,083 A | 6/1993 | Drane et al. |
| 5,217,028 A | 6/1993 | Dutcher et al. |
| 5,223,226 A | 6/1993 | Wittmar et al. |
| 5,230,337 A | 7/1993 | Dahl et al. |
| 5,235,976 A | 8/1993 | Spinelli |
| 5,242,430 A | 9/1993 | Arenas et al. |
| 5,243,980 A | 9/1993 | Mehra |
| 5,255,693 A | 10/1993 | Dutcher et al. |
| 5,259,394 A | 11/1993 | Bens |
| 5,259,395 A | 11/1993 | Li |
| 5,261,395 A | 11/1993 | Oleen et al. |
| 5,261,400 A | 11/1993 | Bardy |
| 5,265,600 A | 11/1993 | Adams et al. |
| 5,269,300 A | 12/1993 | Kelly et al. |
| 5,269,319 A | 12/1993 | Schulte et al. |
| 5,271,417 A | 12/1993 | Swanson et al. |
| 5,271,935 A | 12/1993 | Franco et al. |
| 5,275,620 A | 1/1994 | Darby et al. |
| 5,275,621 A | 1/1994 | Mehra |
| 5,279,293 A | 1/1994 | Andersen et al. |
| 5,282,836 A | 2/1994 | Kreyenhagen et al. |
| 5,282,838 A | 2/1994 | Hauser et al. |
| 5,282,845 A | 2/1994 | Bush et al. |
| 5,284,136 A | 2/1994 | Hauck et al. |
| 5,285,780 A | 2/1994 | Tsuji et al. |
| 5,300,106 A | 4/1994 | Dahl et al. |
| 5,300,108 A | 4/1994 | Rebell et al. |
| 5,300,110 A | 4/1994 | Latterell et al. |
| 5,301,677 A | 4/1994 | Hsung |
| 5,304,219 A | 4/1994 | Chernoff et al. |

| | | | | | | |
|---|---|---|---|---|---|---|
| 5,306,292 A | 4/1994 | Lindegren | | 5,456,699 A | 10/1995 | Armstrong |
| 5,314,448 A | 5/1994 | Kroll et al. | | 5,456,706 A | 10/1995 | Pless et al. |
| 5,314,459 A | 5/1994 | Swanson et al. | | 5,456,708 A | 10/1995 | Doan et al. |
| 5,314,462 A | 5/1994 | Heil et al. | | 5,458,621 A | 10/1995 | White et al. |
| 5,314,464 A | 5/1994 | KenKnight et al. | | 5,458,622 A | 10/1995 | Alt |
| 5,318,597 A | 6/1994 | Hauck et al. | | 5,464,429 A | 11/1995 | Hedberg et al. |
| 5,324,315 A | 6/1994 | Grevious | | 5,466,245 A | 11/1995 | Spinelli et al. |
| 5,324,327 A | 6/1994 | Cohen | | 5,466,253 A | 11/1995 | Doan |
| 5,330,504 A | 7/1994 | Somerville et al. | | 5,469,859 A | 11/1995 | Tsoglin et al. |
| 5,330,508 A | 7/1994 | Gunderson | | 5,470,342 A | 11/1995 | Mann et al. |
| 5,330,512 A | 7/1994 | Hauck et al. | | 5,476,497 A | 12/1995 | Mower et al. |
| 5,331,966 A | 7/1994 | Bennett et al. | | 5,476,499 A | 12/1995 | Hirschberg |
| 5,336,242 A | 8/1994 | Zadeh | | 5,476,501 A | 12/1995 | Stewart et al. |
| 5,339,820 A | 8/1994 | Henry et al. | | 5,476,502 A | 12/1995 | Rubin |
| 5,342,407 A | 8/1994 | Dahl et al. | | 5,480,416 A | 1/1996 | Garcia et al. |
| 5,342,414 A | 8/1994 | Mehra | | 5,480,422 A | 1/1996 | Ben-Haim |
| 5,344,439 A | 9/1994 | Otten | | 5,486,198 A | 1/1996 | Ayers et al. |
| 5,346,506 A | 9/1994 | Mower et al. | | 5,486,202 A | 1/1996 | Bradshaw |
| 5,350,401 A | 9/1994 | Levine | | 5,489,293 A | 2/1996 | Pless et al. |
| 5,350,404 A | 9/1994 | Adams et al. | | 5,492,119 A | 2/1996 | Abrams |
| 5,354,316 A | 10/1994 | Keimel | | 5,496,362 A | 3/1996 | KenKnight et al. |
| 5,358,516 A | 10/1994 | Myers et al. | | 5,500,008 A | 3/1996 | Fain |
| 5,360,442 A | 11/1994 | Dahl et al. | | 5,505,209 A | 4/1996 | Reining |
| 5,366,485 A | 11/1994 | Kroll et al. | | 5,507,780 A | 4/1996 | Finch |
| 5,366,496 A | 11/1994 | Dahl et al. | | 5,513,644 A | 5/1996 | McClure et al. |
| 5,370,124 A | 12/1994 | Dissing et al. | | 5,514,161 A | 5/1996 | Limousin |
| 5,370,663 A | 12/1994 | Lin | | 5,514,172 A * | 5/1996 | Mueller ...................... 607/122 |
| 5,370,667 A | 12/1994 | Alt | | 5,514,174 A | 5/1996 | Heil, Jr. et al. |
| 5,374,281 A | 12/1994 | Kristall et al. | | 5,515,848 A | 5/1996 | Corbett, III et al. |
| 5,374,282 A | 12/1994 | Nichols et al. | | 5,522,853 A | 6/1996 | Kroll |
| 5,374,286 A | 12/1994 | Morris | | 5,522,874 A | 6/1996 | Gates |
| 5,376,103 A | 12/1994 | Anderson et al. | | 5,524,338 A | 6/1996 | Martyniuk et al. |
| 5,376,104 A | 12/1994 | Sakai et al. | | 5,527,344 A | 6/1996 | Arzbaecher et al. |
| 5,379,776 A | 1/1995 | Murphy et al. | | 5,529,579 A | 6/1996 | Alt et al. |
| 5,383,907 A | 1/1995 | Kroll | | 5,531,780 A | 7/1996 | Vachon |
| 5,383,908 A | 1/1995 | Sweeney et al. | | 5,531,781 A | 7/1996 | Alferness et al. |
| 5,385,574 A | 1/1995 | Hauser et al. | | 5,534,022 A | 7/1996 | Hoffmann et al. |
| 5,387,233 A | 2/1995 | Alferness et al. | | 5,540,723 A | 7/1996 | Ideker et al. |
| 5,391,189 A | 2/1995 | van Krieken et al. | | 5,545,188 A | 8/1996 | Bradshaw et al. |
| 5,391,190 A | 2/1995 | Pederson et al. | | 5,545,201 A | 8/1996 | Helland et al. |
| 5,391,199 A | 2/1995 | Ben-Haim | | 5,545,202 A | 8/1996 | Dahl et al. |
| 5,391,200 A | 2/1995 | KenKnight et al. | | 5,545,205 A | 8/1996 | Schulte et al. |
| 5,393,929 A | 2/1995 | Yagihashi | | 5,549,650 A | 8/1996 | Bornzin et al. |
| 5,397,342 A | 3/1995 | Heil, Jr. et al. | | 5,554,178 A | 9/1996 | Dahl et al. |
| 5,403,355 A | 4/1995 | Alt | | 5,571,162 A | 11/1996 | Lin |
| 5,403,356 A | 4/1995 | Hill et al. | | 5,571,163 A | 11/1996 | Helland |
| 5,405,373 A | 4/1995 | Petersson et al. | | 5,578,062 A | 11/1996 | Alt et al. |
| 5,409,009 A | 4/1995 | Olson | | 5,578,068 A | 11/1996 | Laske et al. |
| 5,411,525 A | 5/1995 | Swanson et al. | | 5,593,433 A | 1/1997 | Spehr et al. |
| 5,411,527 A | 5/1995 | Alt | | 5,603,732 A | 2/1997 | Dahl et al. |
| 5,411,544 A | 5/1995 | Mar et al. | | 5,607,455 A | 3/1997 | Armstrong |
| 5,413,593 A | 5/1995 | Spinelli et al. | | 5,609,613 A | 3/1997 | Woodson et al. |
| 5,417,221 A | 5/1995 | Sickler | | 5,620,451 A | 4/1997 | Rosborough |
| 5,423,326 A | 6/1995 | Wang et al. | | 5,620,469 A | 4/1997 | Kroll |
| 5,425,748 A | 6/1995 | Pless | | 5,628,778 A | 5/1997 | Kruse et al. |
| 5,425,755 A | 6/1995 | Doan | | 5,628,779 A | 5/1997 | Bornzin et al. |
| 5,425,756 A | 6/1995 | Heil, Jr. et al. | | 5,632,766 A | 5/1997 | Hsu |
| 5,431,649 A | 7/1995 | Mulier et al. | | 5,634,829 A | 6/1997 | Kerul |
| 5,431,682 A | 7/1995 | Hedberg | | 5,641,326 A | 6/1997 | Adams |
| 5,431,685 A | 7/1995 | Alt | | 5,643,328 A | 7/1997 | Cooke et al. |
| 5,431,693 A | 7/1995 | Schroeppel | | 5,643,338 A | 7/1997 | Bornzin et al. |
| 5,433,730 A | 7/1995 | Alt | | 5,645,082 A | 7/1997 | Sung et al. |
| 5,433,735 A | 7/1995 | Zanakis et al. | | 5,654,030 A | 8/1997 | Munshi et al. |
| 5,435,316 A | 7/1995 | Kruse | | 5,662,687 A | 9/1997 | Hedberg et al. |
| 5,439,391 A | 8/1995 | McEtchin et al. | | 5,662,698 A | 9/1997 | Altman et al. |
| 5,439,483 A | 8/1995 | Duong-Van | | 5,674,272 A | 10/1997 | Bush et al. |
| 5,441,518 A | 8/1995 | Adams et al. | | 5,674,274 A | 10/1997 | Morgan et al. |
| 5,441,521 A | 8/1995 | Hedberg | | 5,681,514 A | 10/1997 | Woody |
| 5,443,073 A | 8/1995 | Wang et al. | | 5,683,429 A | 11/1997 | Mehra |
| 5,443,485 A | 8/1995 | Housworth et al. | | 5,683,443 A | 11/1997 | Munshi et al. |
| 5,447,533 A | 9/1995 | Vachon et al. | | 5,683,447 A | 11/1997 | Bush et al. |
| 5,447,534 A * | 9/1995 | Jammet ...................... 607/127 | | 5,685,322 A | 11/1997 | Sung et al. |
| 5,456,263 A | 10/1995 | Andersen | | 5,699,014 A | 12/1997 | Haefner et al. |

| | | | | | | |
|---|---|---|---|---|---|---|
| 5,700,283 | A | 12/1997 | Salo | 6,123,084 | A | 9/2000 | Jandak et al. |
| 5,709,753 | A | 1/1998 | Olson et al. | H1905 | H | 10/2000 | Hill |
| 5,713,924 | A | 2/1998 | Min et al. | 6,141,594 | A | 10/2000 | Flynn et al. |
| 5,713,926 | A | 2/1998 | Hauser et al. | 6,152,954 | A | 11/2000 | Scheiner et al. |
| 5,716,390 | A * | 2/1998 | Li .............................. 607/127 | 6,165,164 | A | 12/2000 | Hill et al. |
| 5,718,241 | A | 2/1998 | Ben-Haim et al. | 6,212,434 | B1 | 4/2001 | Scheiner et al. |
| 5,718,720 | A | 2/1998 | Prutchi et al. | 6,254,573 | B1 | 7/2001 | Haim et al. |
| 5,720,099 | A | 2/1998 | Parker et al. | 6,309,370 | B1 | 10/2001 | Haim et al. |
| 5,720,768 | A | 2/1998 | Verboven-Nelissen | 6,321,122 | B1 | 11/2001 | Scheiner et al. |
| 5,725,559 | A | 3/1998 | Alt et al. | 6,345,204 | B1 | 2/2002 | Scheiner et al. |
| 5,725,810 | A | 3/1998 | Brunner et al. | 6,358,247 | B1 | 3/2002 | Altman et al. |
| 5,728,140 | A | 3/1998 | Salo et al. | 6,363,286 | B1 | 3/2002 | Zhu et al. |
| 5,730,125 | A | 3/1998 | Prutchi et al. | 6,416,510 | B1 | 7/2002 | Altman et al. |
| 5,730,142 | A | 3/1998 | Sun et al. | 6,463,334 | B1 | 10/2002 | Flynn et al. |
| 5,738,096 | A | 4/1998 | Ben-Haim | 6,501,990 | B1 | 12/2002 | Sundberg et al. |
| 5,749,911 | A | 5/1998 | Westlund | 6,501,994 | B1 | 12/2002 | Janke et al. |
| 5,755,761 | A | 5/1998 | Obino | 6,505,082 | B1 | 1/2003 | Scheiner et al. |
| 5,755,764 | A | 5/1998 | Schroeppel | 6,540,725 | B1 | 4/2003 | Ponzi |
| 5,755,766 | A | 5/1998 | Chastain et al. | 6,575,931 | B1 | 6/2003 | Ponzi |
| 5,759,202 | A | 6/1998 | Schroeppel | 6,623,473 | B1 | 9/2003 | Ponzi |
| 5,766,042 | A | 6/1998 | Ries et al. | 6,623,474 | B1 | 9/2003 | Ponzi |
| 5,769,881 | A | 6/1998 | Schroeppel et al. | 6,702,777 | B2 | 3/2004 | Haim et al. |
| 5,772,604 | A | 6/1998 | Langberg et al. | 6,855,124 | B1 | 2/2005 | Gonzalez et al. |
| 5,772,693 | A | 6/1998 | Brownlee | 6,905,476 | B2 | 6/2005 | Ponzi |
| 5,776,072 | A | 7/1998 | Hsu et al. | 6,909,920 | B2 | 6/2005 | Lokhoff et al. |
| 5,782,876 | A | 7/1998 | Flammang | 6,915,169 | B2 | 7/2005 | Flynn et al. |
| 5,782,879 | A | 7/1998 | Rosborough et al. | 6,931,286 | B2 | 8/2005 | Sigg et al. |
| 5,782,884 | A | 7/1998 | Stotts et al. | 6,983,185 | B2 * | 1/2006 | Ley et al. .................... 607/122 |
| 5,782,898 | A | 7/1998 | Dahl et al. | 2001/0031986 | A1 | 10/2001 | Hauck |
| 5,792,183 | A | 8/1998 | Esler | 2002/0010492 | A1 | 1/2002 | Donovan et al. |
| 5,792,205 | A | 8/1998 | Alt et al. | 2002/0022863 | A1 | 2/2002 | Hauck |
| 5,797,878 | A | 8/1998 | Bleam | 2002/0026228 | A1 | 2/2002 | Schauerte |
| 5,797,967 | A | 8/1998 | KenKnight | 2002/0058981 | A1 | 5/2002 | Zhu et al. |
| 5,800,466 | A | 9/1998 | Routh et al. | 2002/0183720 | A1 | 12/2002 | Hill et al. |
| 5,800,495 | A | 9/1998 | Machek et al. | 2003/0069625 | A1 * | 4/2003 | Ley et al. .................... 607/122 |
| 5,814,088 | A | 9/1998 | Paul et al. | 2003/0093104 | A1 | 5/2003 | Bonner et al. |
| 5,817,130 | A | 10/1998 | Cox et al. | 2003/0109914 | A1 | 6/2003 | Westlund et al. |
| 5,836,985 | A | 11/1998 | Rostami et al. | 2003/0163184 | A1 | 8/2003 | Scheiner et al. |
| 5,837,006 | A | 11/1998 | Ocel et al. | 2003/0171723 | A1 | 9/2003 | Ponzi |
| 5,840,025 | A | 11/1998 | Ben-Haim | 2003/0195470 | A1 | 10/2003 | Ponzi |
| 5,840,079 | A | 11/1998 | Warman et al. | 2004/0122484 | A1 | 6/2004 | Hatlestad et al. |
| 5,843,153 | A | 12/1998 | Johnston et al. | 2004/0186546 | A1 | 9/2004 | Mandrusov et al. |
| 5,843,154 | A | 12/1998 | Osypka | 2004/0213770 | A1 | 10/2004 | Seward et al. |
| 5,851,227 | A | 12/1998 | Spehr | 2005/0137671 | A1 | 6/2005 | Liu et al. |
| 5,855,594 | A | 1/1999 | Olive et al. | 2006/0089698 | A1 | 4/2006 | Sundberg et al. |
| 5,871,529 | A | 2/1999 | Bartig et al. | | | | |
| 5,871,531 | A | 2/1999 | Struble | | | FOREIGN PATENT DOCUMENTS | |
| 5,871,532 | A | 2/1999 | Schroeppel | DE | | 2827595 | 4/1979 |
| 5,876,353 | A | 3/1999 | Riff | DE | | 2949782 A1 | 6/1981 |
| 5,876,431 | A | 3/1999 | Spehr et al. | DE | | 3712082 | 10/1988 |
| 5,881,732 | A | 3/1999 | Sung et al. | EP | | 0042551 | 12/1981 |
| 5,885,221 | A | 3/1999 | Hsu et al. | EP | | 0057877 | 8/1982 |
| 5,908,447 | A | 6/1999 | Schroeppel et al. | EP | | 0211166 | 2/1987 |
| 5,916,214 | A * | 6/1999 | Cosio et al. ................ 606/41 | EP | | 0282047 A | 9/1988 |
| 5,916,238 | A | 6/1999 | Hauser et al. | EP | | 0326290 | 8/1989 |
| 5,916,243 | A | 6/1999 | KenKnight et al. | EP | | 0337035 | 10/1989 |
| 5,921,979 | A | 7/1999 | Kovac et al. | EP | | 0452278 | 10/1991 |
| 5,925,045 | A | 7/1999 | Reimels et al. | EP | | 0460324 | 12/1991 |
| 5,925,069 | A | 7/1999 | Graves et al. | EP | | 0573275 | 12/1993 |
| 5,925,073 | A | 7/1999 | Chastain et al. | EP | | 519053 | 4/1994 |
| 5,935,159 | A | 8/1999 | Cross, Jr. et al. | EP | | 0612538 | 8/1994 |
| 5,944,710 | A | 8/1999 | Dev et al. | EP | | 0620024 | 10/1994 |
| 5,964,757 | A | 10/1999 | Ponzi | EP | | 0680771 | 8/1995 |
| 5,964,795 | A | 10/1999 | McVenes et al. | EP | | 0672431 | 9/1995 |
| 5,972,416 | A | 10/1999 | Reimels et al. | EP | | 709111 A2 | 5/1996 |
| 5,978,705 | A | 11/1999 | KenKnight et al. | EP | | 0813886 | 12/1997 |
| 6,007,476 | A | 12/1999 | Wascher et al. | FR | | 2465489 | 9/1980 |
| 6,024,739 | A | 2/2000 | Ponzi et al. | FR | | 2575925 | 7/1986 |
| 6,055,457 | A | 4/2000 | Bonner | FR | | 2588758 | 4/1987 |
| 6,085,119 | A | 7/2000 | Scheiner et al. | FR | | 2757773 | 12/1996 |
| 6,096,069 | A | 8/2000 | Bischoff | GB | | 2032278 | 6/1980 |
| 6,097,986 | A | 8/2000 | Janke et al. | GB | | 2240721 | 8/1991 |
| 6,119,043 | A | 9/2000 | Hsu et al. | | | | |

| | | |
|---|---|---|
| JP | 3-168161 | 7/1991 |
| JP | 4-40966 | 2/1992 |
| WO | WO-89/06148 | 7/1989 |
| WO | WO-92/20401 | 4/1991 |
| WO | WO-92/07616 | 5/1992 |
| WO | WO-94/22525 | 4/1993 |
| WO | WO-93/20888 | 10/1993 |
| WO | WO-95/08365 | 3/1995 |
| WO | WO-97/40883 | 4/1996 |
| WO | WO-96/15665 | 5/1996 |

OTHER PUBLICATIONS

"Implant Attaches to Bone by Chemical Bond", *Medical Materials Update*, vol. 4, No. 7, (Aug. 1997), pp. 1 and 5.

"Victrex's PEEK Used for Dialysis Machines", *Medical Material's Update*, vol. 3, No. 3, (Apr. 1996), pp. 1-2.

Al-Khadra, A., et al., "The Role of Electroporation in Defibrillation", *Circulation Research*, 87(9), (Oct. 2000), 797-804.

Ayers Gregory M., et al., "Ventricular Proarrhythmic Effects of Ventricular Cycle Length and Shock Strength in a Sheep Model of Transvenous Atrial Defibrillation", *Circulation*, 89 (1), (Jan. 1994), 413-422.

Barton, A. J., et al., "Bacterial Adhesion to Orthopedic Implant Polymers", *J. Biomed. Mat. Res.*, 30(3), (Mar. 1996), 403-410.

Fain, et al., "A New Internal Defibrillation Lead System: Intrapericardial Placement Without Thoracotomy", *Circulation Supplement*, 76 (4), Abstracts from the 60th Scientific Sessions, Abstract No. 1839,(Oct. 1987), 1 p.

Feeser, S. A., et al., "Strength-duration and probability of success curves for defibrillation with biphasic waveforms", *Circulation*, 82(6), (Dec. 1990), 2128-2141.

Genc, S., et al., "Methodology for Locking Feature Selection in Integral Snap-Fit Assembly", *Proceedings of DETC '97, 1997 ASME Engineering Technical Conferences*, (Sep. 1997), 1-11.

Ha. S. W., et al., "Plasma-Sprayed Hydroxylapatite Coating on Carbon Fibre Reinforced Thermoplastic Composite Materials", *J. Mater. Sci. Mater. Med.*, vol. 5, No. 6-7, (1994), pp. 481-484.

Jockisch, K. A., et al., "Biological Response to Chopped-Carbon-Fiber-Reinforced Peek", *J. Biomed. Mater. Res.*, vol. 26, No. 2, (1992), pp. 133-146.

Jones, D. L., et al., "Internal Cardiac Defibrillation in Man: Pronounced Improvement with Sequential Pulse Delivery to Two Different Lead Orientations", *Circulation*, 73(3), (Mar. 1986), 484-491.

Kanno, S., et al., "Establishment of a simple and practical procedure applicable to therapeutic angiogenesis", *Circulation*, 99(20), (May 25, 1999),2682-2687.

Knapp, Christopher P., et al., "Snap Fit Terminal Connector", U.S. Appl. No. 09/184,226, filed Nov. 2, 1998, 39.

Labhasetwar, V., et al., "Iontophoresis for Modulation of Cardiac Drug Delivery in Dogs", *Proceedings of the National Academy of Sciences USA*, 92(7), (Mar. 28, 1995), 2612-2616.

Lin, T. W., et al., "Glass Peek Composite Promotes Proliferation and Osteocalcin of Human Osteoblastic Cells", *J. Biomed. Mater. Res.*, vol. 36, No. 2, (1997),pp. 137-144.

Liu, Lili, "His Bundle Mapping, Pacing, and Injection Method and Lead", U.S. Appl. No. 10/745,302, filed Dec. 23, 2003, 41 pgs.

Macnair, R., et al., "The Response of Primary Rat and Human Osteoblasts and an Immortalized Rat Osteoblast Cell Line to Orthopaedic Materials: Comparative Sensitivity of Several Toxicity Indices", *J. Mater. Sci. Mater. Med.*, vol. 8, No. 2, (1997),pp. 105-111.

Meyer, M. R., et al., "Long-Term Durability of the Interface in FRP Composites After Exposure to Simulated Physiologic Saline Environments", *J. Biomed. Mater. Res.*, vol. 28, No. 10, (1994),pp. 1221-1231.

Morrison, C., et al., "In Vitro Biocompatibility Testing of Polymers for Orthopaedic Implants Using Cultured Fibroblasts and Osteoblasts", *Biomaterials*, vol. 16, No. 13, (1995),pp. 987-992.

Singer, Igor, et al., "The Automatic Implantable Cardioverter Defibrillator: T Wave Sensing in the Newest Generation", *PACE*, 11, Part I,(Nov. 1988),pp. 1584-1591.

Soyer, J., et al., "Experimental Characterisation of a Carbon/PEEK Hip Prothesis in Fatigue", *Chirurgie*, 121, (1996),p. 658-663.

Tang. A. S., et al., "Three-Dimensional Potential Gradient Fields Generated by Intracardiac Catheter and Cutaneous Patch Electrodes", *Circulation*, 85 (5), (May 1992), pp. 1857-1864.

Thakor, N. V., et al., "Optimal QRS Detector", *Medical & Biological Engineering & Computing*, 21, (May 1983),pp. 343-350.

Wenz, L. M., et al., "In Vitro Biocompatibility of Polyetheretherketone and Polysulfone Composites", *J. Biomed. Mater. Res.*, vol. 26, No. 2, (1990), pp. 207-215.

US 6,875,206, 04/2005, Ponzi (withdrawn)

* cited by examiner

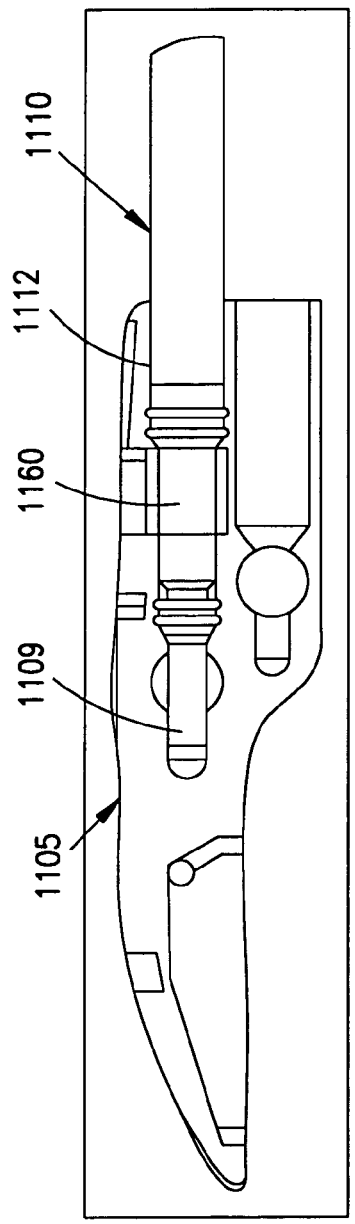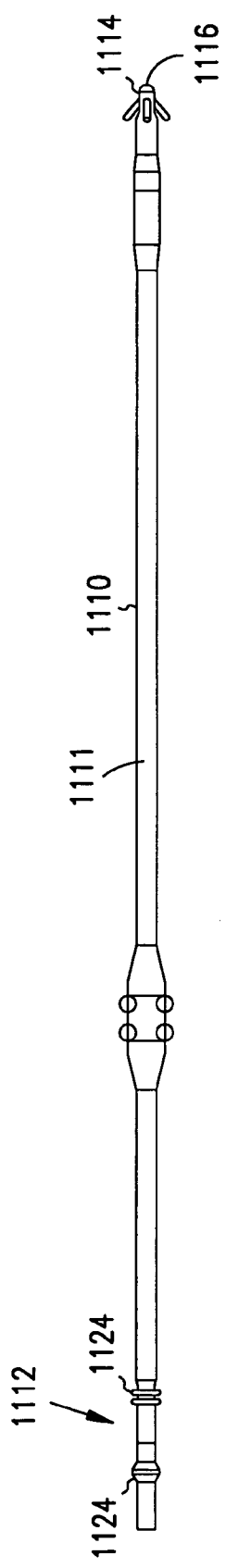
FIG. 7C
FIG. 7B

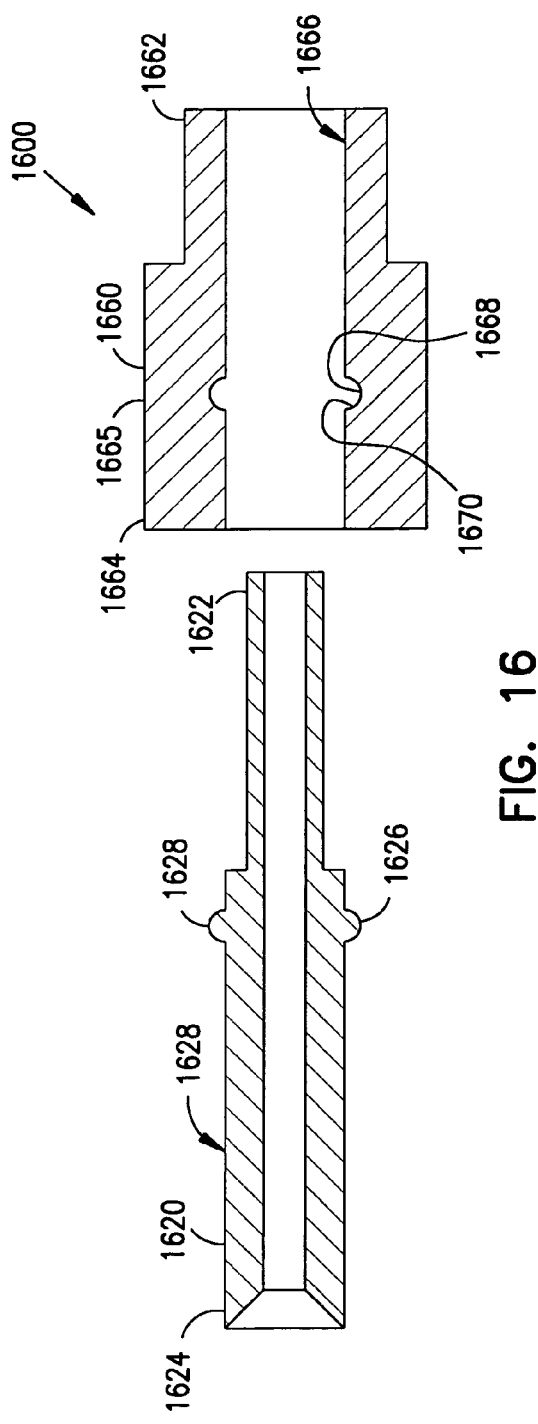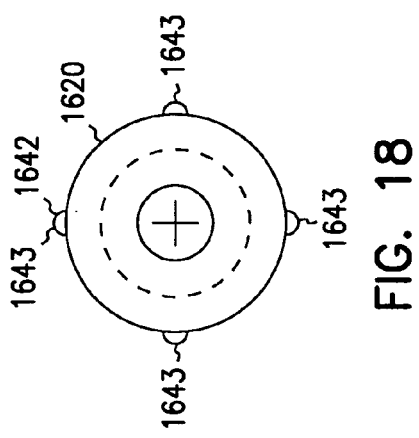

EXTENDABLE AND RETRACTABLE LEAD HAVING A SNAP-FIT TERMINAL CONNECTOR

CROSS-REFERENCE TO RELATED APPLICATION(S)

This patent application is a continuation of U.S. patent application Ser. No. 10/264,494, filed Oct. 4, 2002, now issued as U.S. Pat. No. 6,915,169, which is a division of U.S. patent application Ser. No. 09/359,580, filed on Jul. 22, 1999, now issued as U.S. Pat. No. 6,463,334, which is a continuation-in-part of U.S. patent application Ser. No. 09/121,005, filed on Jul. 22, 1998, now U.S. Pat. No. 6,141,594, U.S. patent application Ser. No. 09/120,824, filed on Jul. 22, 1998, now issued as U.S. Pat. No. 6,212,434, and U.S. patent application Ser. No. 09/184,226, filed on Nov. 2, 1998, now abandoned, each of which is assigned to a common assignee and the specifications of which are incorporated herein by reference in their entirety.

Additionally, this patent application is related to U.S. patent application Ser. No. 09/472,098, filed on Dec. 23, 1999 now issued as U.S. Pat. No. 6,501,990 and U.S. patent application Ser. No. 10/210,192, filed on Jul. 31, 2002, now issued as U.S. Pat. No. 6,983,185 each of which is assigned to a common assignee, and the specifications of which are incorporated herein by reference in their entirety.

FIELD OF THE INVENTION

The present invention relates generally to implantable leads. More particularly, it pertains to leads having an extendable and retractable fixation mechanism.

BACKGROUND OF THE INVENTION

Electrodes have been used to stimulate contraction of the heart or to reverse certain life threatening arrhythmias, where electrical energy is applied to the heart via the electrodes to return the heart to normal rhythm. Electrodes have also been used to sense and deliver pacing pulses to the atrium and ventricle. Cardiac pacing may be performed by a transvenous method or by electrodes implanted directly onto the epicardium. For transvenous pacing systems, a lead having an electrode is positioned in the right ventricle and/or in the right atrium through a subclavian vein, and the proximal electrode terminals are attached to a pacemaker which is implanted subcutaneously.

Some lead designs have "floating" electrodes or electrodes which are not attached to the endocardial wall of the heart. The floating electrodes lay in the blood pool or against the endocardial wall of the heart and the electrode may move slightly within the heart. Since the location of floating electrodes is not fixed with respect to the endocardial wall, the electrical performance of these electrodes varies and is generally less than optimal. Both the electrical sensing capability as well as the pacing delivery capability of such electrodes are suboptimal. The pacing parameters of such a floating electrode are also suboptimal. In addition, the floating electrodes can require increased voltage which unnecessarily drains the battery.

As an alternative to floating electrodes, leads have been provided with passive fixation elements that affix the electrode to the endocardial wall over time. With passive fixation elements, it can be difficult to determine whether the lead will affix in the location at which it is implanted.

Active fixation elements, such as a helix, have also been provided with distal ends of leads which allow a lead to be affixed to the endocardial wall. The helix is rotated to screw the lead into the endocardial wall. To rotate the helix toward and into the endocardial wall, a stylet is disposed within the lead and rotated. As the stylet is rotated however, the active fixation element may jump out of the end of the lead and damage tissue, and/or the helix. In addition, it is difficult for the implanter to determine how many turns to the stylet is necessary to advance the helix a certain distance.

A cardiac pacing system typically includes a pulse generator which supplies the electrical energy to the lead. The pulse generator may be implanted into a subcutaneous pocket made in the wall of the chest. A lead coupled with the pulse generator is routed subcutaneously from the pocket to the shoulder or neck where the lead enters a major vein, such as the subclavian vein, and into the heart. The proximal end of the lead is coupled both electrically and mechanically with the pulse generator at A distal end of the lead is placed within the heart, and a proximal end is placed within a pacemaker.

When leads with multiple conductors are involved, the conductors are individually and electrically coupled with the pulse generator at a proximal end of the multiple conductors. The multiple conductors at the proximal end are electrically insulated from each other to prevent shorts and limit electrical leakage between conductors. Medical adhesive is used to insulate the multiple conductors at the proximal end of the lead. However, the process of using medical adhesive is timely and costly to assemble. In addition, the medical adhesive bonds inconsistently, sometimes resulting in mechanical and electrical separation between the components.

The proximal end of the lead includes a terminal connection which provides the electrical and mechanical connection between the pacemaker and the proximal end of the lead. When inserted into the pacemaker, the components of the terminal connection undergoes axial stress as the implanter forces the proximal end of the lead into the pacemaker. After inserted, the implanter may pull on the lead to ensure the terminal end is sufficiently seated in the pacemaker, placing additional axial stress on the terminal connection.

Accordingly, there is a need for a lead with multiple conductors which are reliably insulated from one another. What is further needed is a lead having a terminal connection which can accommodate axial stress placed thereon.

SUMMARY OF THE INVENTION

An extendable and retractable lead includes a lead body which extends from a distal end to a proximal end. A conductor is disposed within the lead body and extends from the distal end to the proximal end of the lead body. In addition, the lead includes an electrode base coupled with the conductor proximate to the distal end of the lead body. The electrode base is threadingly coupled with an outer threaded shell. The electrode base includes external threads disposed thereon. The lead also includes an active fixation element coupled with the electrode base and the outer threaded shell.

In one embodiment, the lead includes a movement assembly which is configured to extend and retract the active fixation mechanism. The movement assembly includes a housing having an internally threaded portion and an externally threaded collar which is engaged with the internally threaded portion. In another embodiment, the movement assembly further includes an internally threaded insert disposed within the lead, where the threaded collar is engaged with the threaded insert.

In yet another embodiment, the outer threaded shell is formed of polyetheretherketone. Alternatively, the lead further includes a second outer shell coupled with the outer threaded shell, where the second outer shell forms a stop for the electrode base. In one embodiment, the second outer shell is formed of polyetheretherketone. The outer threaded shell is coupled with the second outer shell, for example, with epoxy. The epoxy comprises, in one embodiment, a mixture of one part EPOTEK 353ND to 1.75 parts EPOTEK 353ND-T. In yet another embodiment, the lead further includes a fluoroscopic ring disposed about the fixation helix.

A lead includes a lead body extending from a distal end to a proximal end. At least one conductor is disposed within the lead body and extends from the distal end to the proximal end of the lead body. An outer terminal ring is coupled with the lead body, and a sleeve is coupled with the outer terminal ring, and is also coupled with a terminal pin. The coupling allows for rotational movement between the outer terminal ring and the terminal pin. The sleeve is coupled with the outer terminal ring or the terminal pin with a snap-fit coupling. The snap-fit coupling, in one embodiment, comprises a first and second set of cantilevered hooks. In another embodiment, the snap-fit coupling comprises an annular flange received in a recess.

In another embodiment, a lead is provided which includes a lead body extending from a distal end to a proximal end. At least one conductor is disposed within the lead body and extends from the distal end to the proximal end of the lead body. An outer terminal ring is coupled with the lead body, and a sleeve is coupled with the outer terminal ring, and is also coupled with a terminal pin. The sleeve is coupled with the terminal pin with a snap-fit connection.

In yet another embodiment, a lead is provided which includes a lead body extending from a distal end to a proximal end. At least one conductor is disposed within the lead body and extends from the distal end to the proximal end of the lead body. An outer terminal ring is coupled with the lead body, and a sleeve is coupled with the outer terminal ring, and is also coupled with a terminal pin. The sleeve is coupled with the outer terminal ring or the terminal pin with a press-fit coupling.

A lead includes, in another embodiment, a lead body which is coupled with an outer terminal ring. The outer terminal ring is coupled with a terminal pin with a snap-fit connection. An insulator is disposed between the outer terminal ring and the terminal pin, and in one embodiment comprises a non-conductive coating. In one embodiment, the outer terminal ring is rotatably coupled with the terminal pin.

In yet another embodiment, a system includes an electronics system which has a pulse generator. The pulse generator is electrically coupled with a lead which includes a lead body extending from a distal end to a proximal end. At least one conductor is disposed within the lead body and extends from the distal end to the proximal end of the lead body. An outer terminal ring is coupled with the lead body, and a sleeve is coupled with the outer terminal ring, and is also coupled with a terminal pin. The coupling allows for rotational movement between the outer terminal ring and the terminal pin. The sleeve is coupled with the outer terminal ring or the terminal pin with a snap-fit coupling. The snap-fit coupling, in one embodiment, comprises a first and second set of cantilevered hooks. In another embodiment, the snap-fit coupling comprises an annular flange received in a recess. In yet another embodiment, the lead further includes a movement assembly which is configured to extend and retract an active fixation mechanism. The movement assembly includes a housing having an internally threaded portion and an externally threaded collar which is engaged with the internally threaded portion. In another embodiment, the movement assembly further includes an internally threaded insert disposed within the lead, where the threaded collar is engaged with the threaded insert.

The lead assembly described above provides several advantages, for example, ease of manufacturability is increased and through put times are reduced. The individual components can be snapped together, as opposed to waiting for messy bonding or long cure times. Bonding blocks, used for the bonding process, are eliminated, which are expensive, difficult and costly to clean. A consistent and increased strength of coupling is achieved using the snap fit design since bonding is variable based on the operator. Yet another advantage is that the geometry of the snap fit connector provides an insulation with a known thickness, which allows for a repeatable dielectric strength.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 7B is an elevational view of an example of a lead for use in the system shown in FIG. 7A.

FIG. 7C is a cross-sectional view of a lead coupled with a pulse generator constructed in accordance with one embodiment.

FIG. 16 is an exploded cross-sectional view of an assembly constructed in accordance with one embodiment.

FIG. 17 is a cross-sectional view of an assembly constructed in accordance with one embodiment.

FIG. 18 is a cross-sectional view of an assembly constructed in accordance with another embodiment.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
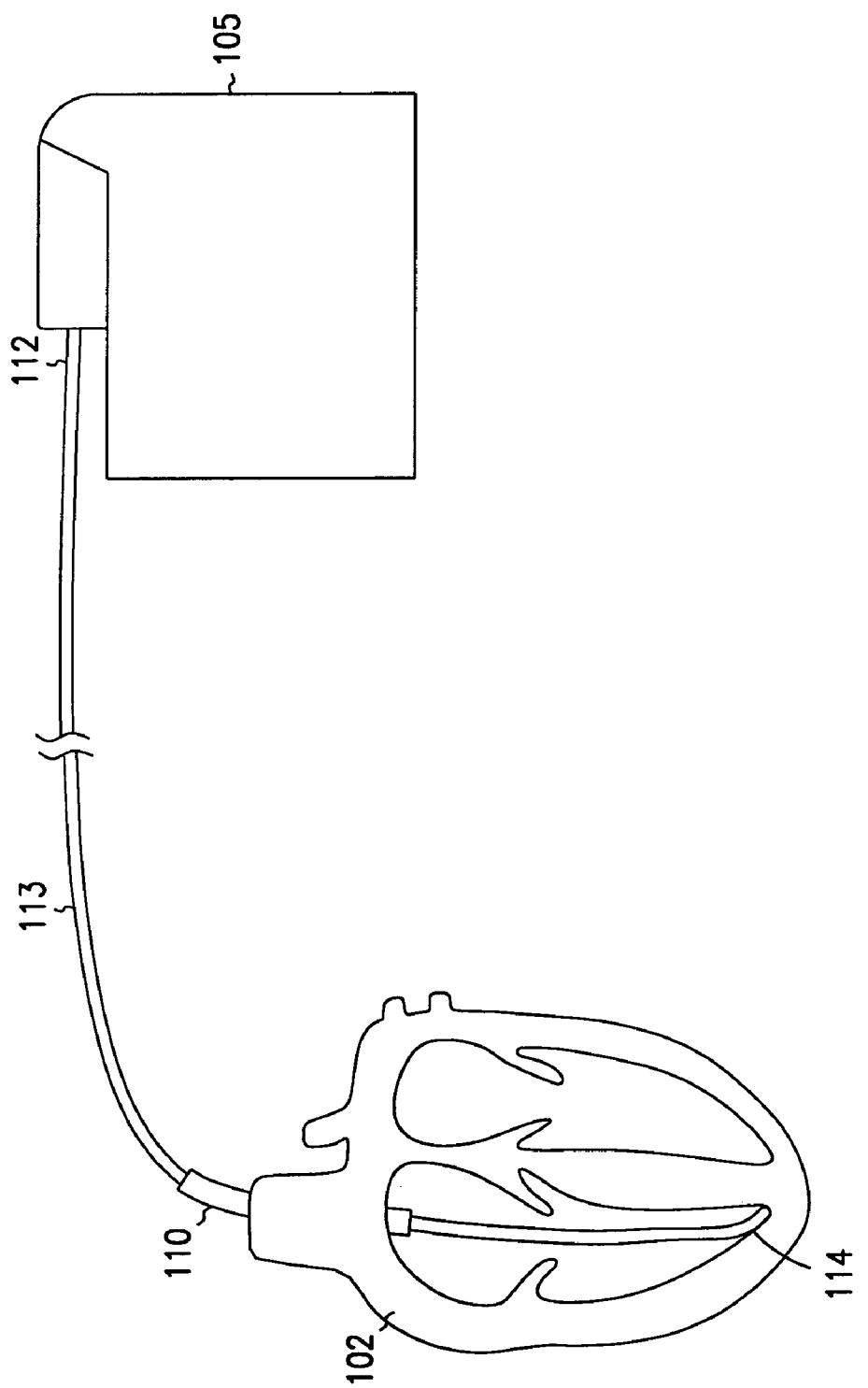
FIG. 1 is a block diagram illustrating a system for delivering and/or receiving signals to and from the heart constructed in accordance with one embodiment.

An extendable and retractable lead 110 and lead system 100 are illustrated in FIG. 1. FIG. 1 is a block diagram of a system 100 for delivering and/or receiving electrical pulses or signals to stimulate and/or sense the heart 102. The system 100 includes a pulse generator 105 and a lead 110. The pulse generator 105 includes a source of power as well as an electronic circuitry portion. The pulse generator 105 is a battery-powered device which generates a series of timed electrical discharges or pulses. The pulse generator 105 is generally implanted into a subcutaneous pocket made in the wall of the chest. Alternatively, the pulse generator 105 is placed in a subcutaneous pocket made in the abdomen, or in other locations.

The lead 110 includes a lead body 113 which extends from a proximal end 112, where it is coupled with the pulse generator 105, as further discussed below. The lead 110 extends to a distal end 114, which is coupled with a portion of a heart 102, when implanted. The distal end 114 of the lead 110 includes at least one electrode 116 (FIG. 2) which electrically couples the lead 110 with the heart 102. At least one electrical conductor 118 (FIG. 2) is disposed within the lead 110 and extends from the proximal end 112 to the distal end 114 of the lead 110. The at least one electrical conductor 118 electrically couples the electrode 116 with the proximal end 112 of the lead 110. The electrical conductors carry electrical current and pulses between the pulse generator 105 and the electrode 116.

Figure 2:
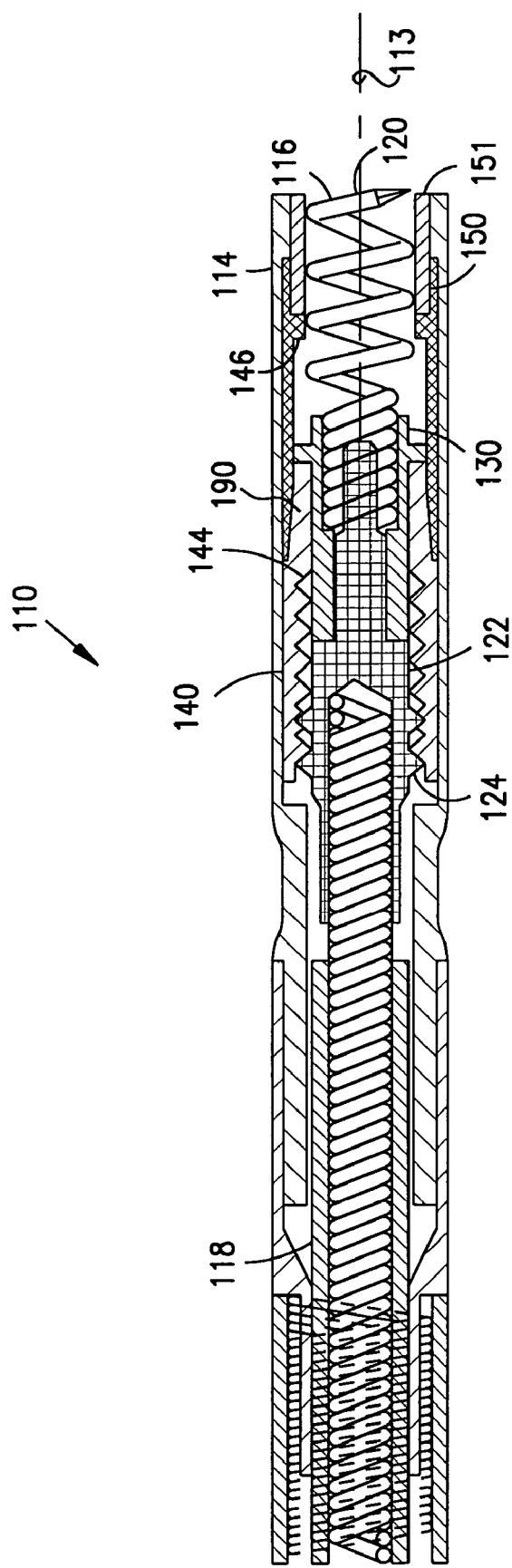
FIG. 2 is a cross-section illustrating a terminal end of a lead constructed in accordance with one embodiment.
Figure 3:
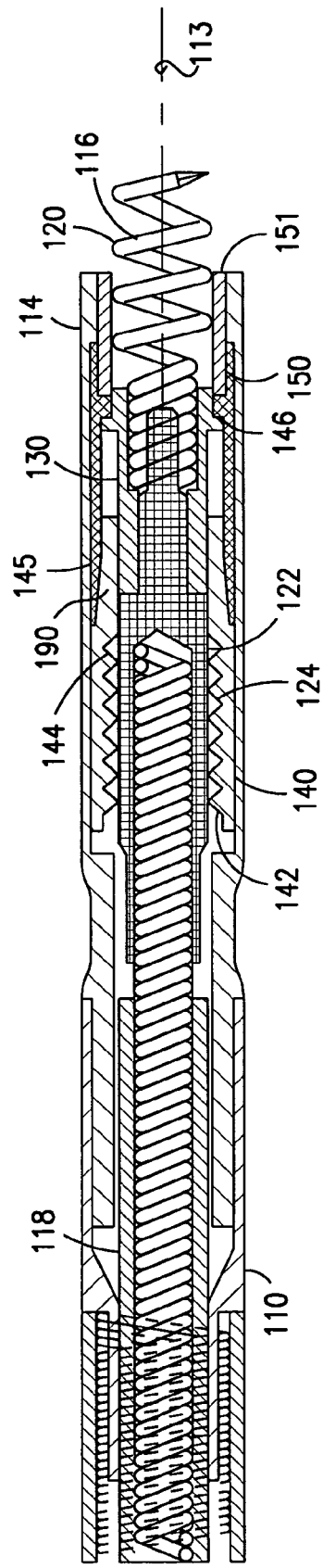
FIG. 3 is a cross-section illustrating a distal end of a lead constructed in accordance with one embodiment.

FIGS. 2 and 3 illustrate one embodiment of the distal end 114 of the lead 110 in greater detail, where FIG. 2 illustrates the lead 110 in a retracted position and FIG. 3 illustrates the lead 110 in an extended position. The electrode 116 comprises a fixation helix 120 which allows for the distal end 114 of the lead 110 to be affixed to the heart 102 (FIG. 1). The fixation helix 120 is mechanically and electrically coupled with an electrode base 122. The electrode base 122 is mechanically coupled with the at least one electrical conductor 118, such that as the conductor 118 is rotated, the electrode base 122 translates along an axis 113 of the lead 110, as will be further discussed below. In one embodiment, the electrode base 122 is electrically coupled with the at least one electrical conductor 118, and the electrode base 122 is formed of an electrically conductive material, such as metal. Disposed about the electrode base 122 are external threads 124, which allow the electrode base 122 to rotate and translate the fixation helix 120. The electrode base 122 is coupled with an outer threaded shell 140. In one embodiment, a steroid collar 151 is disposed within the distal end 114 of the lead 110.

The threaded shell 140 has internal threads 142 therein. The internal threads 142 provide a path for the external threads 124 of the electrode base 122. As the electrode base 122 is rotated, the external threads 124 engage with the internal threads 142 and translate the electrode base 122 along the axis 113 of the lead 110. In one embodiment, the lead 110 includes a stop to prevent the fixation helix 120 from overextension. The stop comprises, in one embodiment, a stop 144 on the internal threads 142 which blocks the rotation of the external threads 124. Once the external threads 124 reach the stop 144, the electrode base 122 can no longer be rotated and translated out of the lead 110, which prevents the fixation helix 120 from being overextended into tissue of, for example, a heart. In another embodiment, the stop comprises a stop 146 formed on an outer shell 145 which is disposed adjacent to the electrode collar 130 (discussed below).

The outer threaded shell 140 and/or the outer shell 145, in one embodiment, is formed of polyetheretherketone (PEEK). In another embodiment, the outer threaded shell 140 is formed of PEEK 150G, low melt viscosity. For the PEEK 150G, the melt viscosity ranges from about 0.12-0.18 KNs/m$^2$, and the tensile strength is greater than or equal to 90 MPa. The threaded shell 140, in another embodiment, comprises PEEK 450G, standard melt viscosity. For the PEEK 450G, the melt viscosity ranges from about 0.38-0.50 KNs/m$^2$, and the tensile strength is greater than or equal to 90 MPa. The PEEK allows for the outer threaded shell 140 to be molded, extruded, or machined for tighter tolerances or providing precision structures. PEEK is a tough rigid thermoplastic material which is biocompatible.

Proximate to the distal end 114 of the lead 110 is a fluoroscopy ring 150, which is disposed about the fixation helix 120. The electrode base 122 has, in one embodiment, an electrode collar 130 coupled therewith, such that as the electrode base 122 is translated, the electrode collar 130 translates along the axis 113. As the fixation helix 120 is extended out from the lead 110, the electrode collar 130 translates toward the fluoroscopy ring 150 until the electrode collar 130 abuts a portion the fluoroscopy ring 150, at which point the fixation helix 120 is fully extended. The collar 130 and the ring 150 allows the implanter to view, under fluoroscopy, when the fixation helix 120 is fully extended.

As discussed above, the outer shell 145, provides a stop for the translation of the electrode collar 130. The outer shell 145 is coupled with the outer threaded shell 140. Epoxy 190, in one embodiment, is disposed between the outer threaded shell 140 and the outer shell 145. In one embodiment, the epoxy 190 comprises a blend of two different epoxies. The two different epoxies are EPOTEK® 353ND and EPOTEK® 353ND-T made by Epoxy Technology. The two epoxies are mixed in the ratio of 1 part EPOTEK® 353ND to 1.75 parts EPOTEK® 353ND-T. The epoxy is cured at a temperature of 150° C. for one hour.

Figure 4:
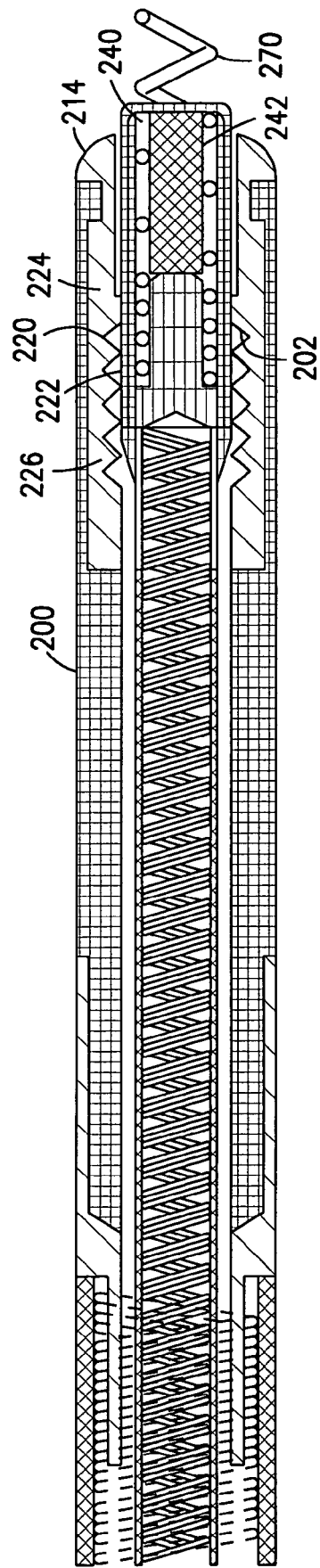
FIG. 4 is a cross-section illustrating a distal end of a lead constructed in accordance with another embodiment.
Figure 5:
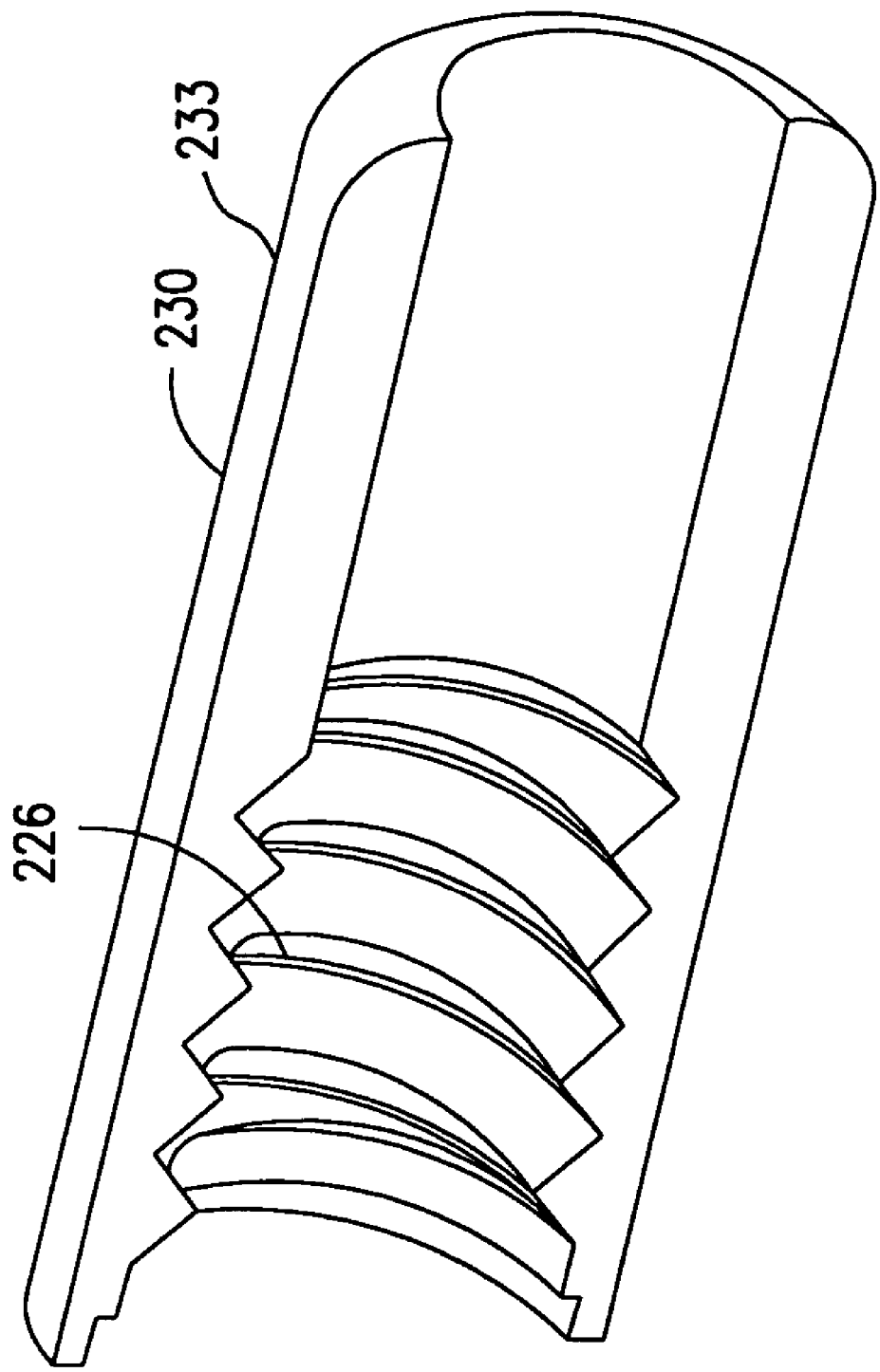
FIG. 5 is a cross-section illustrating a distal end of a lead constructed in accordance with another embodiment.

FIGS. 4 and 5 illustrate another embodiment of a lead 200. The lead 200 includes a retractable active fixation element 270, which assists in avoiding injury to the patient during implantation. Alternatively, the active fixation element 270 rotates without translating along the lead 200. The lead 200 further includes a movement assembly 202 disposed at a distal end 214 of the lead 200, where the movement assembly 202 is adapted to transport the active fixation element 270 in and out of the lead 200 as the active fixation element 270 is rotated.

Referring again to FIG. 4, the movement assembly 202 includes external threads 220 associated therewith. In one embodiment, the external threads 220 are disposed about a collar 222 of the lead 200. The external threads 220 are adapted to engage with internal threads 226 disposed within a housing 224 of the lead 200. The internal threads 226 provide a helical path for the external threads 220. The movement assembly 202 is not, however, limited to the components described herein. For instance, the external threads 220 and the internal threads 226 can be provided on alternative components, and still be considered within the scope of the invention. In one embodiment, an insert 230 is provided for the internal threads 226, as shown in FIG. 5. As shown in FIG. 5, the insert 230 comprises a semi-cylindrical collar 233, where the collar 233 is disposed within the lead 200. In another embodiment, a two-piece insert is provided which includes a first half and a second half. The first half and the second half are coupled together to form a cylindrical collar in which there are internal threads. In one embodiment, the first half and the second half are molded from plastic material. In another embodiment, the first half and the second half are machined from, for example, hard plastic materials or metal, or the materials discussed above.

The insert 230 contains internal threads 226 which are adapted to engage with the external threads 220 of the collar 222. During use, a terminal pin (FIG. 6) is rotated which causes the collar 222 to rotate. As the collar 222 is rotated and the external threads 220 and the internals threads 226 engage, the active fixation element 270 moves along the axis 214 of the lead 200. The movement assembly 202 can be used with a wide variety of leads implementing active fixation, including, but not limited to, single pass dual chamber pacing leads, single pass dual chamber pacing/defibrillator leads, single chamber pacing leads, and single chamber pacing/defibrillator leads.

In another embodiment, a mesh screen 240 is provided at a distal end 214 of the lead 200. The mesh screen 240 allows for better tissue in-growth, as well as enhanced sensing capabilities. The mesh screen 240 is disposed proximate to the active fixation element 270. In one embodiment, as the active fixation element 270 is translated and extended from the lead 200, mesh screen 240 moves with the active fixation element 270. The fixation element 270 engages the heart tissue and draws the mesh screen 240 into contact with the surface of the heart. In yet another embodiment, a steroid 242 is disposed within the distal end 214 of the lead 200.

Figure 6:
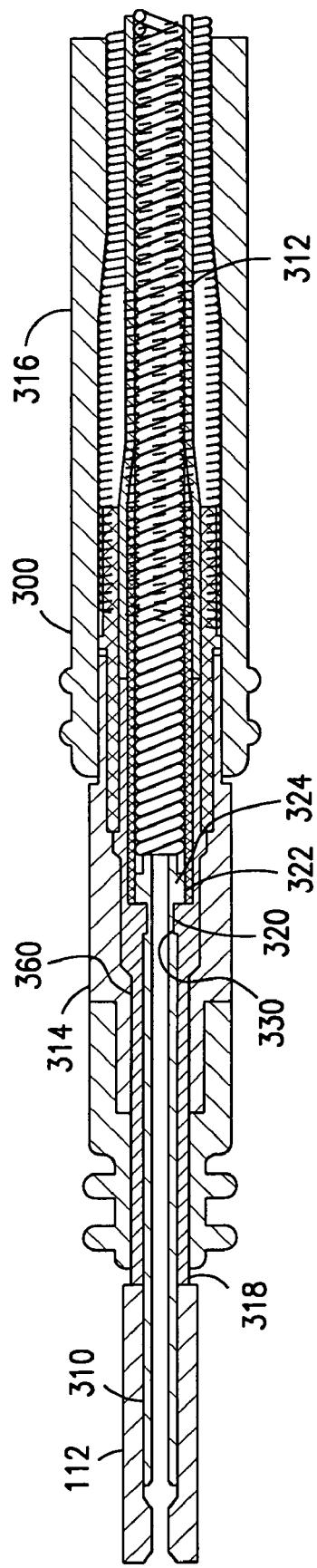
FIG. 6 is a perspective view illustrating a portion of a movement assembly end of a lead constructed in accordance with another embodiment.

FIG. 6 illustrates one embodiment of the proximal end 112 of a lead 300 in greater detail. The lead 300, in one embodiment, incorporates the embodiments discussed for the distal end discussed above and below. In addition, the proximal end 112 of lead 300 includes a terminal pin 310 which provides the electrical connection between the pulse generator 105 (FIG. 1) and the lead 300. The terminal pin 310 is mechanically coupled with a conductor coil 312. As the terminal pin 310 is rotated, the conductor coil 312 rotates, thereby rotating the electrode base (FIGS. 2 and 3) as discussed above.

The lead 300 further includes an outer terminal ring 314 which is coupled with a lead body 316. An insulator sleeve 318 is disposed over at least a portion of the terminal pin 310, and the insulator sleeve 318 insulates the terminal pin 310 from the outer terminal ring 314. In one embodiment, the sleeve 318 is rotatably coupled with the outer terminal ring 314.

The sleeve 318, in another embodiment, is coupled with the terminal pin 310 with a snap-fit connection. Alternatively, the sleeve 318 is coupled with the terminal pin 310 and/or the outer terminal ring 314 with a snap-fit connection. In one embodiment, the sleeve 318 includes at least one projection 320. The at least one projection 320 is engaged with a recess 330 of the terminal pin 310, and prevents the terminal pin 310 from moving axially. The projection 320, in one embodiment, comprises an annular projection disposed about the circumference of the sleeve 318, which allows the terminal pin 310 to rotate relative to the outer terminal ring 314. The annular projection engages within an annular recess disposed within the circumference of the terminal pin 310. In yet another embodiment, the sleeve 318 further includes at least one recess 322 disposed adjacent to the projection 320. The at least one recess 322 receives therein a projection 324 of the terminal pin 310. The additional mating male and female components provide increased axial strength to the connection between the lead 300 and the pulse generator (FIG. 1). In yet another embodiment, the sleeve 318 further includes a stop 360 for the outer terminal ring 314.

The sleeve 318 is formed of non-conductive material. In one embodiment, the sleeve 318 is formed of polyetheretherketone (PEEK). In another embodiment, the sleeve 318 is formed of PEEK 150G, low melt viscosity. For the PEEK 150G, the melt viscosity ranges from about 0.12-0.18 KNs/$m^2$, and the tensile strength is greater than or equal to 90 MPa. The sleeve 318, in another embodiment, comprises PEEK 450G, standard melt viscosity. For the PEEK 450G, the melt viscosity ranges from about 0.38-0.50 KNs/$m^2$, and the tensile strength is greater than or equal to 90 MPa. The PEEK allows for the sleeve 318 to be molded, extruded, or machined for tighter tolerances or providing precision structures. PEEK is a tough rigid thermoplastic material which is biocompatible.

Figure 7A:
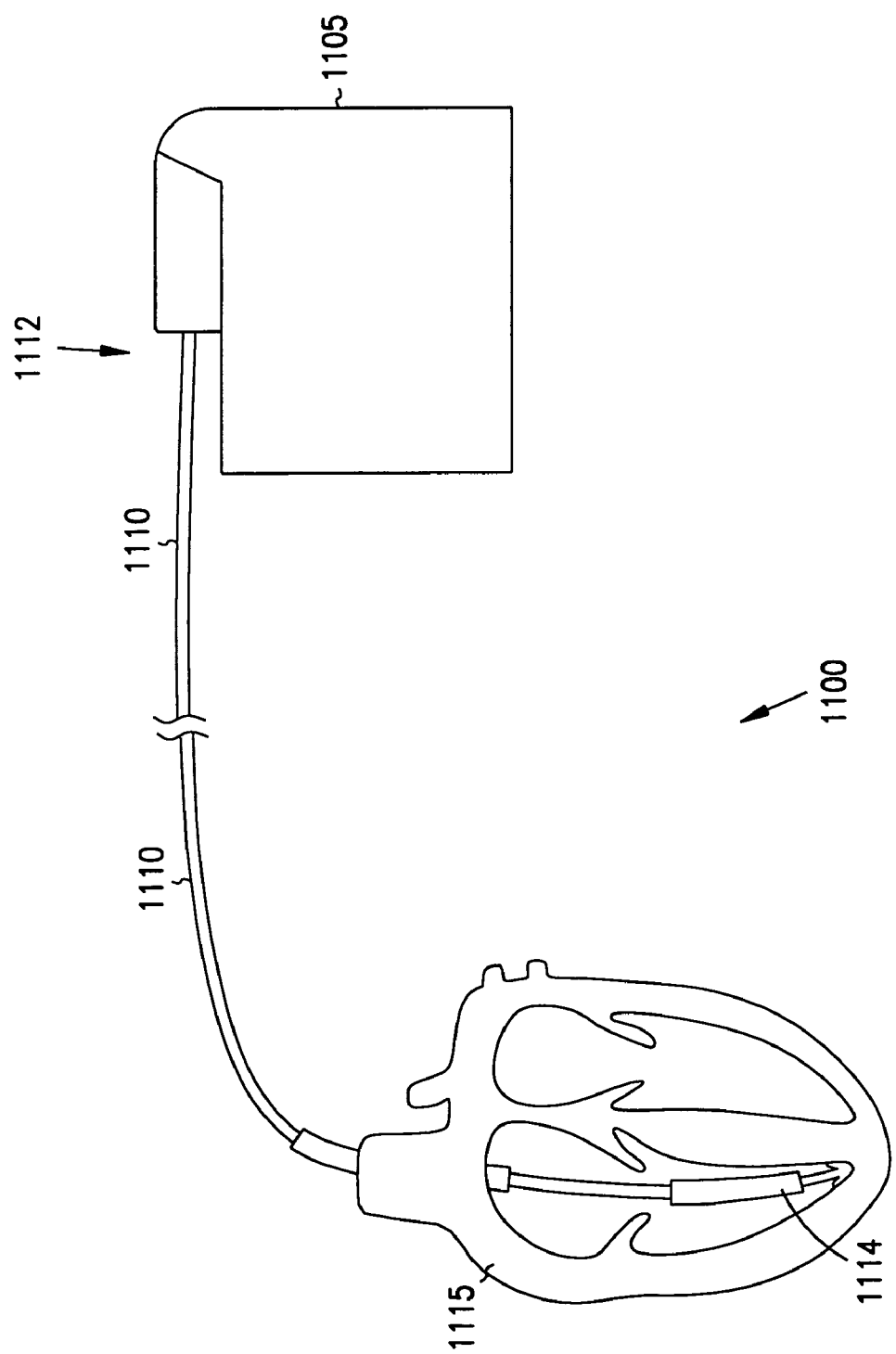
FIG. 7A is a block diagram of a system with a lead for use with a heart and constructed in accordance with one embodiment.

FIGS. 7A-19 illustrate additional embodiments of the lead and lead system. FIG. 7A is a block diagram of a system 1100 for delivering and/or receiving electrical pulses or signals to stimulate and/or sense the heart. The system for delivering pulses 1100 includes a pulse generator 1105 and a lead 1110. The pulse generator 1105 includes a source of power as well as an electronic circuitry portion. The pulse generator 1105 is a battery-powered device which generates a series of timed electrical discharges or pulses used to initiate depolarization of excitable cardiac tissue. The pulse generator 1105 is generally implanted into a subcutaneous pocket made in the wall of the chest. Alternatively, the pulse generator 1105 is placed in a subcutaneous pocket made in the abdomen, or in other locations. An enlargement of the connection between the lead 1110 and the pulse generator 1105 is shown in FIG. 7C, described in more detail below.

The lead 1110, shown in more detail in FIG. 7B, extends from a proximal end 1112, where it is coupled with the pulse generator 1105, and extends to a distal end 1114, which is coupled with a portion of a heart 1115, in the implanted condition (FIG. 7A). The proximal end 1112 of the lead 1110 includes an overmolded portion 1124 which assists in sealing the lead 1110 to the pulse generator 1105. The distal end 1114 of the lead 1110 includes at least one electrode 1116 which electrically couples the lead 1110 with the heart 1115. The electrode 1116 is either a unipolar or bipolar type electrode. In one embodiment, multiple electrodes are provided. At least one electrical conductor (FIG. 9B) is disposed within the lead 1110 and electrically couples the electrode 1116 with the proximal end 1112 of the lead 1110. The electrical conductors carry electrical current and pulses between the pulse generator 1105 and the electrode 1116 located in the distal end 1114 of the lead 1110.

The body 1111 of the lead 1110, in one embodiment, is cylindrical in shape, and is made of a tubing material formed of a biocompatible polymer suitable for implementation within the human body. Although not required, the tubing is made from a silicone rubber type polymer. The lead 1110 travels from the pulse generator 1105 and into a major vein and the distal end 1114 of the lead 1110, in one embodiment, is placed inside the heart 1115. The lead will be either actively or passively affixed to the endocardial wall of a chamber of the heart, depending on the embodiment.

Figure 8:
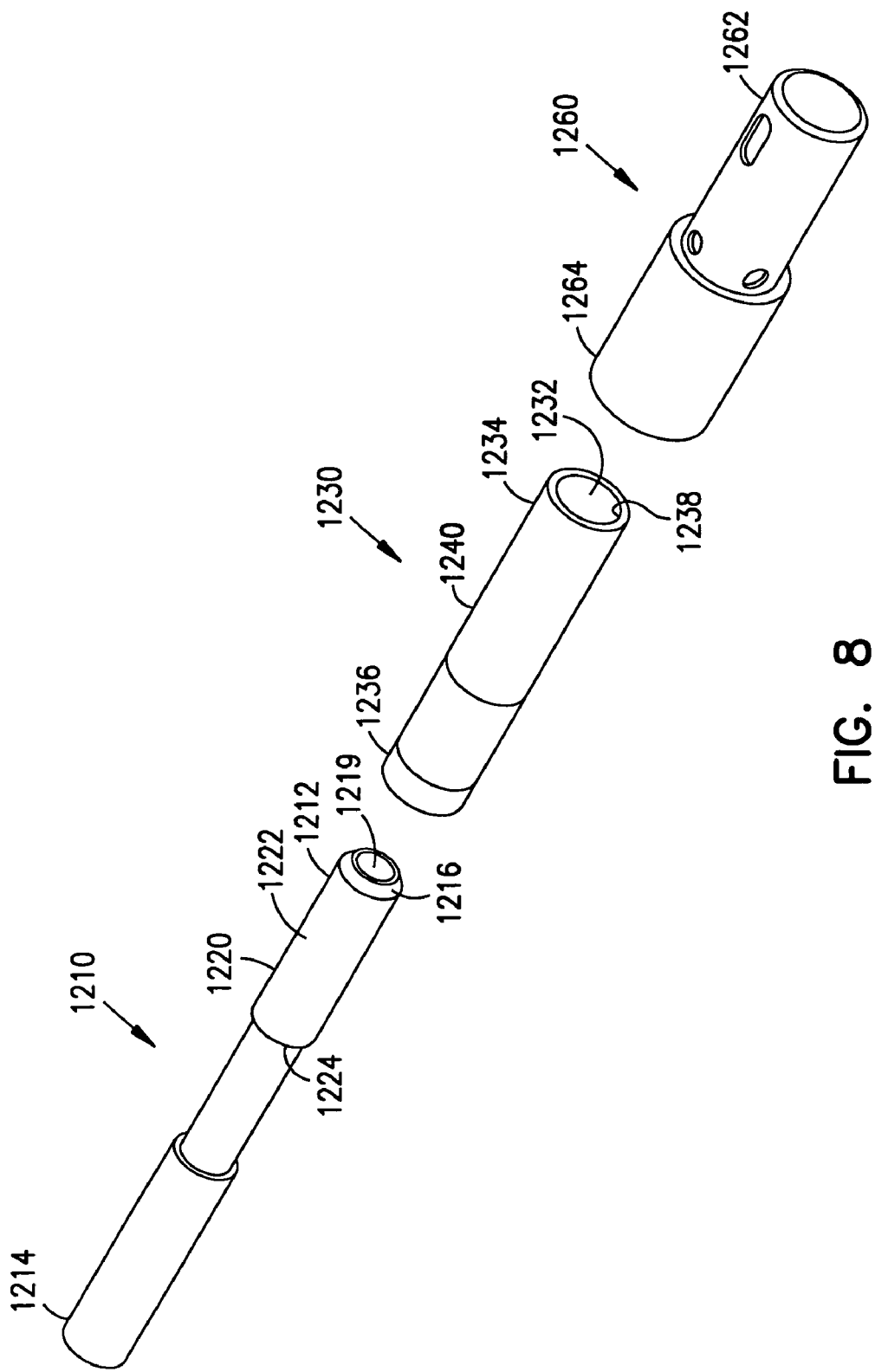
FIG. 8 is an exploded perspective view of an assembly constructed in accordance with one embodiment.
Figure 9A:
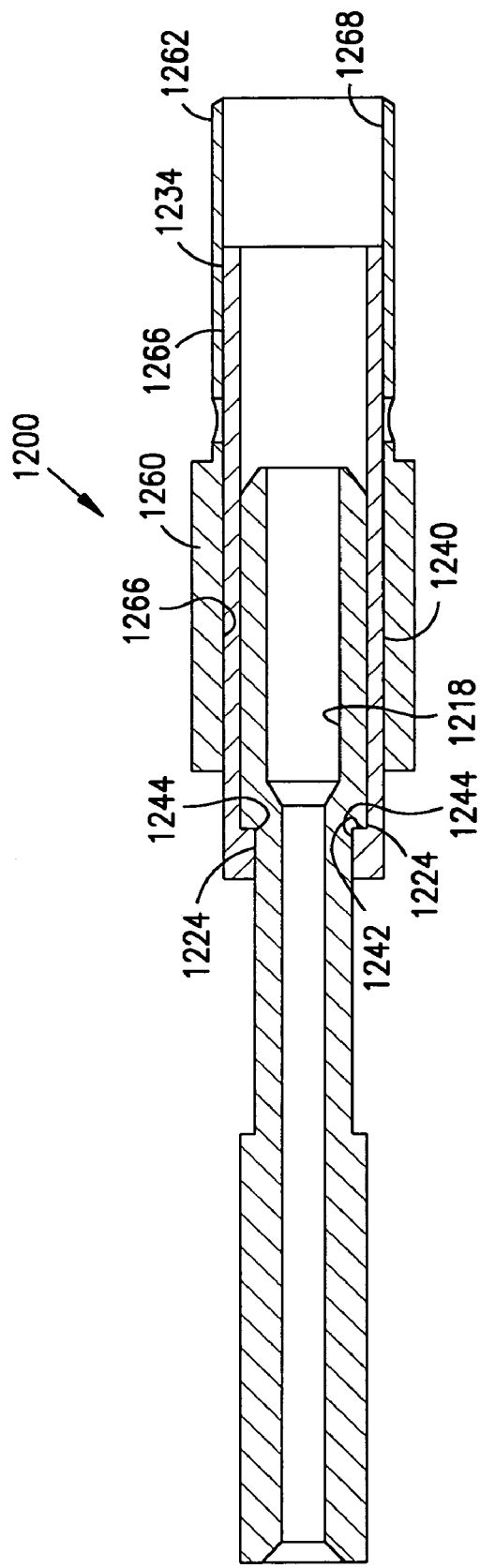
FIG. 9A is an unexploded cross-sectional view of the assembly shown in FIG. 8 constructed in accordance with one embodiment.
Figure 9B:
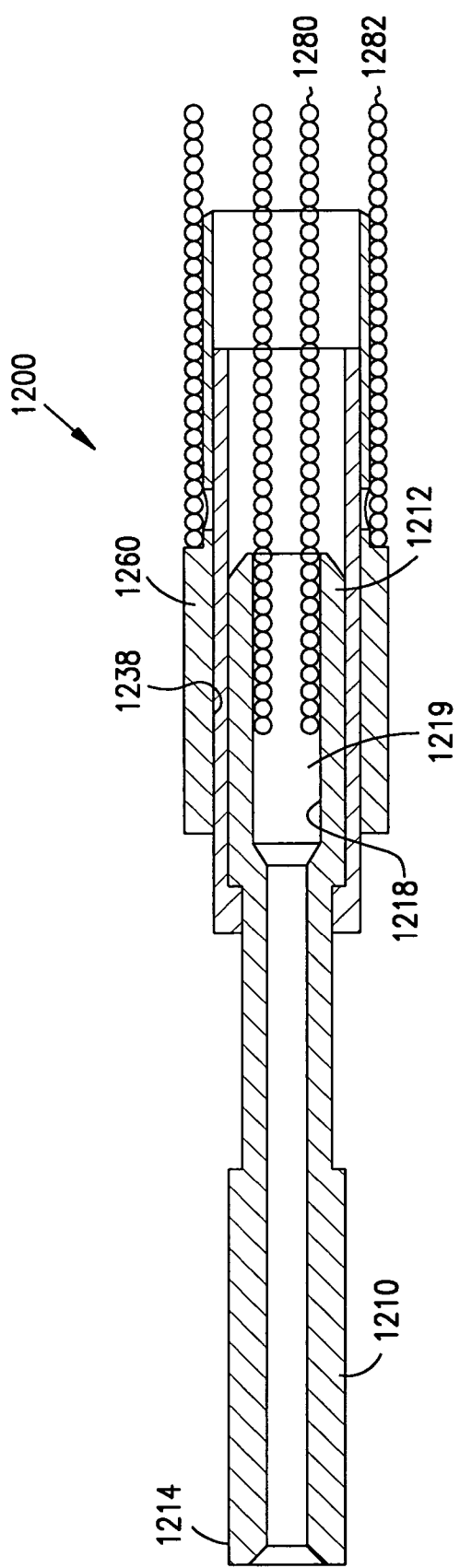
FIG. 9B is a cross-section view of a portion of a lead constructed in accordance with another embodiment.

FIGS. 8, 9A, and 9B illustrate another embodiment of the lead including a press-fit design. The assembly 1200 includes a terminal pin 1210, a sleeve 1230, and an outer terminal ring 1260, which are all coupled together such that, after assembly, axial movement of the individual components is prevented, as further described below. The terminal pin 1210 and the outer terminal ring 1260 each provide an electrical connection in between the lead 1110 and the pulse generator 1105, as shown in FIG. 7C, and as further discussed below. The terminal pin 1210 extends from a first end 1212 to a second end 1214. The second end 1214 is adapted for coupling with the pulse generator 1105, as discussed above (FIGS. 7A and 7C). The first end 1212 is adapted to be inserted into other components of the assembly 1200, specifically the sleeve 1230, as will be further described below. The first end 1212 of the terminal pin 1210 includes a tapered portion 1216 which facilitates insertion of the terminal pin 1210 into the sleeve 1230. In addition, the terminal pin 1210 includes an assembly portion 1220 which is disposed near the first end 1212.

The assembly portion 1220, in one embodiment, includes an outer surface 1222 which extends toward an annular ridge 1224. The outer surface 1222 is adapted to be received within the sleeve 1230, as described below. The outer surface 1222 is tapered from the first end 1212 towards the annular ridge 1224. The annular ridge 1224 forms an engaging surface which is received and retained by the sleeve, as further described below.

The terminal pin 1210 also includes an internal surface 1218 which defines a lumen 1219 therein. The lumen 1219 extends through the terminal pin 1210 from the first end 1212 to the second end 1214 and allows for instruments, such as catheters, stylets, or guidewires, to be inserted through the terminal pin 1210 and through the lead 1110 (FIG. 7B). In addition, the internal surface 1218 of the terminal pin 1210 provides a coupling surface for a first conductor 1280, as illustrated in FIG. 9B, whereat the first conductor 1280 is electrically coupled with the terminal pin 1210. The first conductor 1280 provides an electrical connection between the terminal pin 1210 and an electrode of the lead 1110.

As mentioned above, the assembly 1200 also includes a sleeve 1230. In one embodiment, the sleeve 1230 is an insulator between the terminal pin 1210 and the outer terminal ring 1260, where the sleeve 1230 electrically insulates the terminal pin 1210 from the outer terminal ring 1260. In addition, the sleeve 1230 provides a mechanical connection between the terminal pin 1210 and the outer terminal ring 1260. The sleeve 1230 extends from a first end 1234 to a second end 1236, where the first end 1234 of the sleeve 1230 couples with the outer terminal ring 1260. The second end 1236 is adapted to couple with the terminal pin 1210. Disposed through the sleeve 1230 is a bore 1232, where the bore 1232 is adapted to receive the terminal pin 1210 therein. The bore 1232 allows for instruments, such as catheters, stylets, or guidewires, to be inserted through the sleeve 1230 and through the lead 1110 (FIG. 11B).

The bore 1232 includes an internal surface 1238 which has a coupling feature 1242 thereon. In one embodiment, the coupling feature 1242 includes an annular shoulder 1244. The shoulder 1244 engages the annular ridge 1224 of the terminal pin 1210. The sleeve 1230 also includes an external surface 1240. The external surface 1240, in one embodiment, is engaged by the outer terminal ring 1260, and is tapered. In one embodiment, the taper extends from the second end 1236 toward the first end 1234 of the sleeve 1230.

The assembly 1200 also includes an outer terminal ring 1260 which extends from a first end 1262 to a second end 1264. The outer terminal ring 1260 includes a coupling portion 1266 which is formed, in one embodiment, on an internal surface 1268 of the outer terminal ring 1260. In one embodiment, the internal surface 1268 of the outer terminal ring 1260 is sized to receive the external surface 1240 of the sleeve 1230 therein, such that an interference fit or a press-fit is created thereby. The interference fit between the sleeve 1230 and the outer terminal ring 1260 retains the sleeve 1230 axially to the outer terminal ring 1260.

To assemble the assembly 1200, the first end 1212 of the terminal pin 1210 is inserted into the second end 1236 of the sleeve 1230. The terminal pin 1210 is inserted until the annular ridge 1224 engages with the shoulder 1244 of the sleeve 1230. Once the terminal pin 1210 is coupled with the sleeve 1230, the sleeve 1230 is then coupled with the outer terminal ring 1260 and axial movement between the sleeve 1230 and the outer terminal ring 1260 is prevented. The first end 1234 of the sleeve 1230 is inserted into the second end 1264 of the outer terminal ring 1260. The sleeve 1230 is inserted into the outer terminal ring 1260 until the interference fit is created between the two. Alternatively, in another embodiment, the sleeve 1230 can be assembled first with the outer terminal ring 1260 prior to insertion of the terminal pin 1210 into the sleeve 1230.

The terminal pin 1210 and the outer terminal ring 1260 are both formed from conductive material. The sleeve 1230 is formed from a nonconductive material, and acts as an insulator between the terminal pin 1210 and the outer terminal ring 1260. The sleeve 1230 can be formed from various high-performance engineering plastics, unreinforced and reinforced materials including, but not limited to polysulfone, polyimide, polyamide, polyacetal, polyketone, polyester, polycarbonate, polyolefin, or liquid crystal polymers. Alternatively, the sleeve 1230 is formed from the materials discussed in the above embodiments. These materials are appropriate for the sleeve 1230 described for FIGS. 8 and 9, and also for all of the embodiments discussed above and below.

Figure 10:
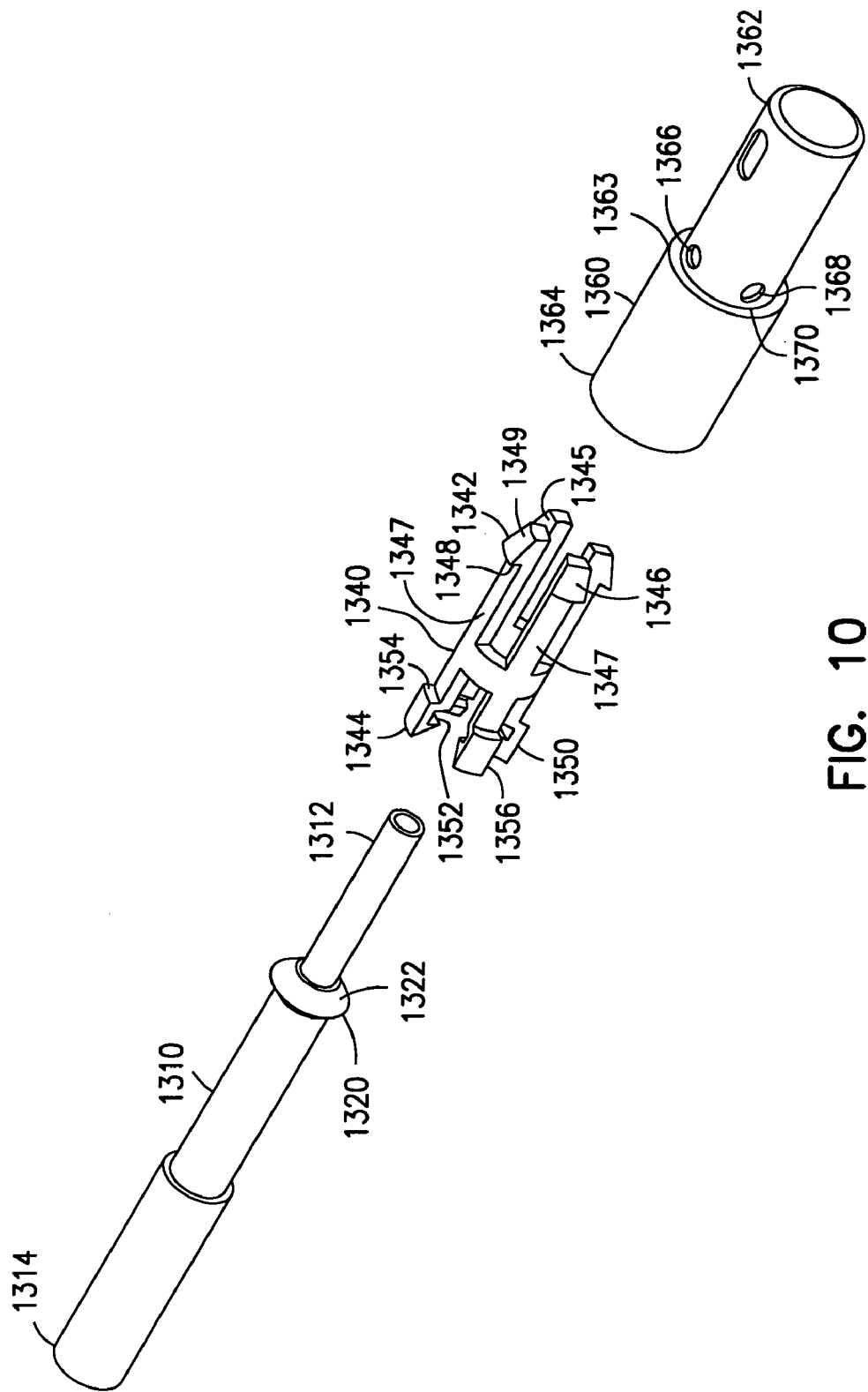
FIG. 10 is an exploded perspective view of an assembly constructed in accordance with another embodiment.
Figure 11:
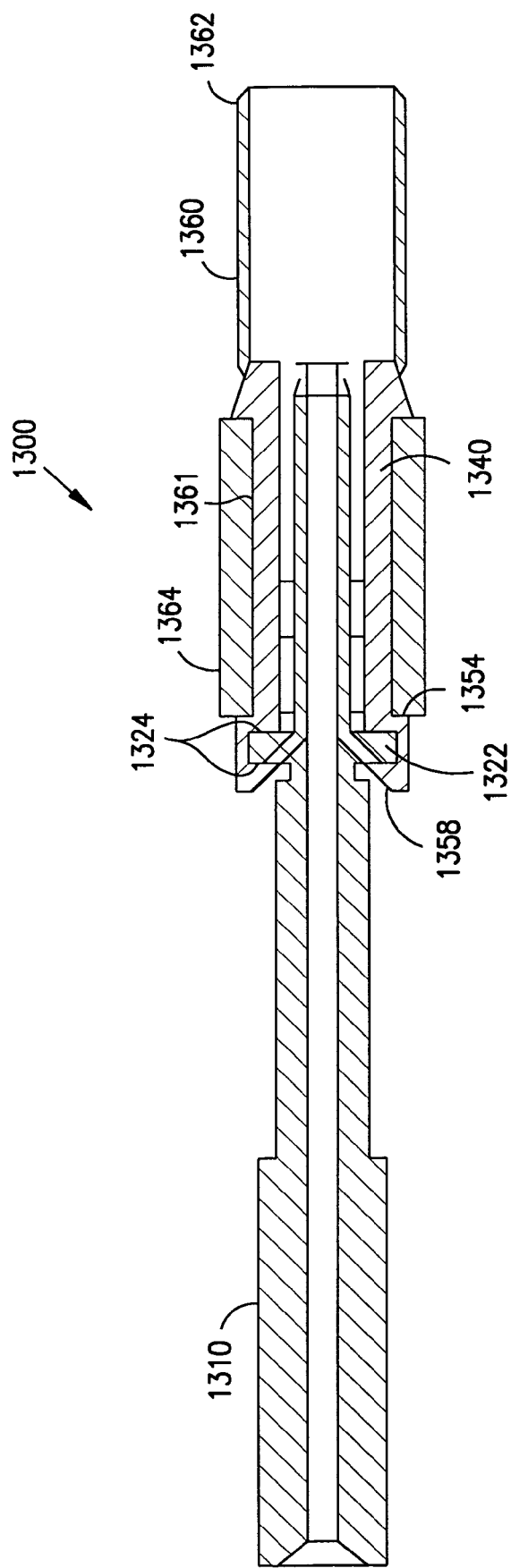
FIG. 11 is an unexploded cross-sectional view of the assembly shown in FIG. 10 constructed in accordance with one embodiment.

FIGS. 10 and 11 illustrate another embodiment of a snap-fit assembly 1300, which generally includes a terminal pin 1310, a sleeve 1340, and an outer terminal ring 1360. The terminal pin 1310 is adapted to be coupled with the pulse generator 1105 as shown in FIG. 7C. The sleeve 1340 is adapted to coupled with the terminal pin 1310 and the outer terminal ring 1360. The terminal pin 1310 extends from a first end 1312 to a second end 1314, and includes a coupling portion 1320 integral therewith. The coupling portion 1320 is formed on an external surface of the terminal pin 1310, and in one embodiment, comprises an annular flange 1322. The annular flange 1322, which can partially or completely encircle the outer surface of the terminal pin 1310, includes mating surfaces 1324 which are adapted to engage with the sleeve 1340, as will be described below.

The sleeve 1340 extends from a first end 1342 to a second end 1344, and includes a first set of coupling features 1345.

The first set of coupling features 1345 are disposed proximate to the first end 1342 of the sleeve 1340. In one embodiment, the first set of coupling features 1345 include a first set of cantilever hooks 1346. The first set of cantilever hooks 1346 are adapted to deflect from a hinge point 1347 and are also adapted to couple with a portion of the outer terminal ring 1360. The first set of cantilever hooks 1346 further include, in another embodiment, mating surfaces 1348. The mating surfaces 1348 are disposed proximate to tapered portions 1349 of the first set of cantilever hooks 1346. It should be noted that the first set of cantilever hooks 1346 refer to a plurality of coupling features, such as cantilever hooks, however, a single cantilever hook can also be used.

Disposed proximate to the second end 1344 of the sleeve 1340 are a second set of coupling features 1356. In one embodiment, the second set of coupling features 1356 comprise a second set of cantilever hooks 1350. The second set of cantilever hooks 1350 are adapted to couple with the coupling portion 1320 of the terminal pin 1310. The second set of cantilever hooks 1350, in another embodiment, each include a recess 1352 formed therein. The recess 1352 of each of the second set of cantilever hooks 1350 is adapted to receive the annular flange 1322 therein. It should be noted that although a second set of cantilever hooks 1350 are described herein, a single cantilever hook can also be used. A tapered ingress 1358 is formed on the second set of cantilever hooks 1350 to facilitate insertion of the terminal pin 1310 therethrough. In yet another embodiment, the sleeve 1340 also includes a positive stop 1354. The positive stop 1354 has a surface which rests against a portion of the outer terminal ring 1360, preventing further movement thereof.

The outer terminal ring 1360, which couples with the sleeve 1340, extends from a first end 1362 to a second end 1364, and has an intermediate portion 1363 therebetween. The outer terminal ring 1360 includes coupling features 1366, which in one embodiment are disposed proximate to the intermediate portion 1363. The coupling features 1366, in another embodiment, include cutouts 1368. The number of cutouts 1368 corresponds to the number of hooks in the first set of cantilever hooks 1346 of the sleeve 1340. The cutouts 1368 also correspond in shape to receive the first set of cantilever hooks 1346 therein. In one embodiment, the cutouts 1368 comprise circular apertures. In another embodiment, the coupling features 1366 each include a mating surface 1370, which is disposed adjacent the mating surfaces 1348 of the sleeve 1340 when the sleeve 1340 is assembled to the outer terminal ring 1360.

To assemble the snap-fit assembly 1300, the terminal pin 1310 is coupled with the sleeve 1340, and the sleeve 1340 is coupled with the outer terminal ring 1360. The terminal pin 1310 can be assembled first into the sleeve 1340, alternatively, the sleeve can first be coupled with the outer terminal ring 1360. To assemble the terminal pin 1310 to the sleeve 1340, the first end 1312 of the terminal pin 1310 is inserted into the second end 1344 of the sleeve 1340. As the terminal pin 1310 is further inserted into the sleeve 1340, the second set of cantilever hooks 1350 are deflected by the annular flange 1322. The terminal pin 1310 is further inserted into the sleeve 1340 until the annular flange 1322 is seated within the recess 1352. The terminal pin 1310 and the sleeve 1340 assembly is then coupled with the outer terminal ring 1360.

The first end 1342 of the sleeve 1340 is inserted into the second end 1364 of the outer terminal ring 1360. As the first end 1342 of the sleeve 1340 is inserted, the first set of cantilever hooks 1346 are deflected. The sleeve 1340 is further inserted into the outer terminal ring 1360 until the tapered portion 1349 of the first set of cantilever hooks 1346 are seated within the cutouts 1368 of the outer terminal ring 1360. The mating surfaces 1348 of the cantilever hooks 1346 are placed adjacent to the mating surface 1370 of the outer terminal ring 1360.

The terminal pin 1310 and the outer terminal ring 1360 are each formed of a conductive material. The sleeve 1340 is formed from a nonconductive material, and acts as an insulator between the terminal pin 1310 and the outer terminal ring 1360, in one embodiment. The sleeve 1340 can be formed from various high-performance engineering plastics, unreinforced and reinforced materials including, but not limited to polysulfone, polyimide, polyamide, polyacetal, polyketone, polyester, polycarbonate, polyolefin, or liquid crystal polymers.

Figure 12:
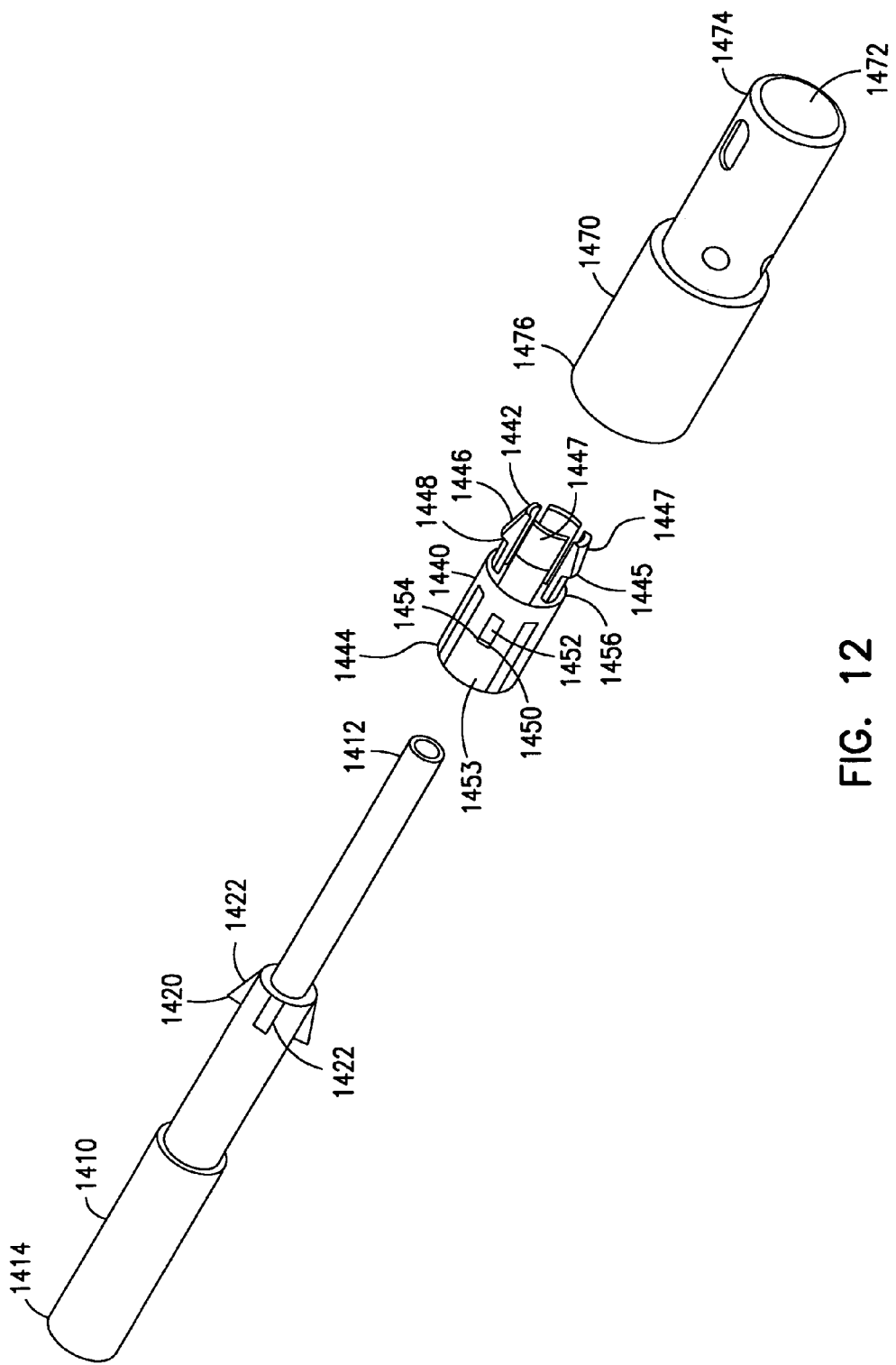
FIG. 12 is an exploded perspective view of an assembly constructed in accordance with yet another embodiment.
Figure 13:
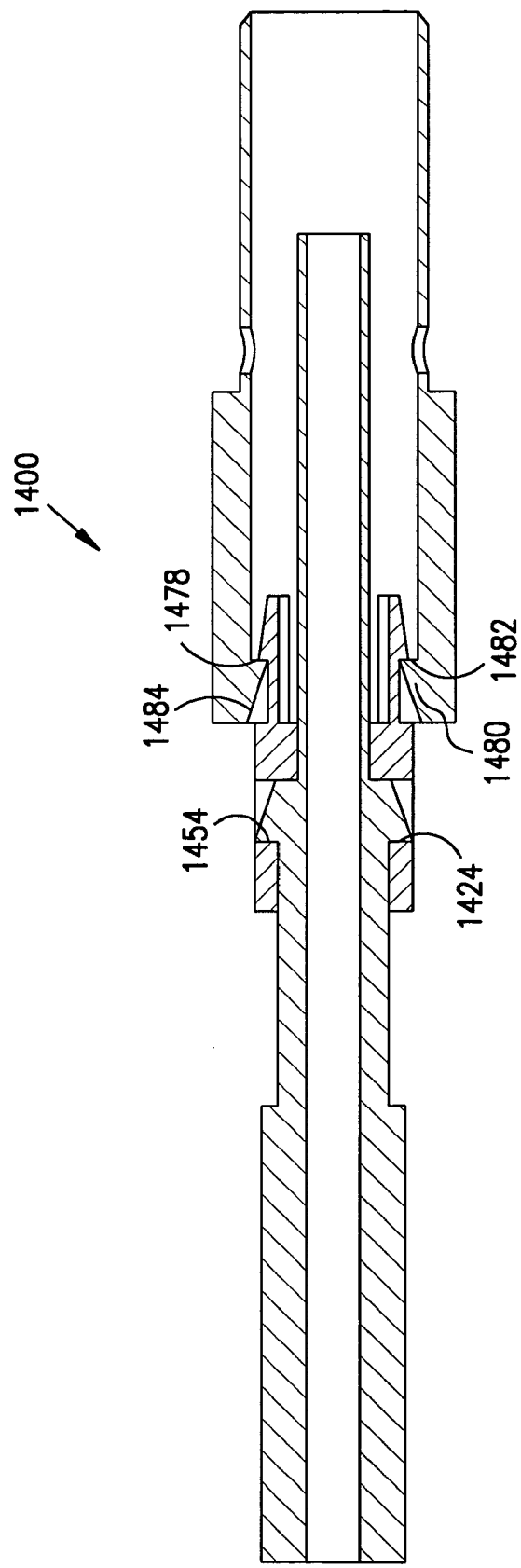
FIG. 13 is an unexploded cross-sectional view of the assembly shown in FIG. 13 constructed in accordance with one embodiment.

FIGS. 12 and 13 illustrate another embodiment of a snap-fit assembly 1400 which generally includes a terminal pin 1410, a sleeve 1440, and an outer terminal ring 1470. The sleeve 1440 is adapted for coupling with the outer terminal ring 1470 and the terminal pin 1410. The terminal pin 1410 extends from a first end 1412 to a second end 1414 and includes a coupling portion 1420. In one embodiment, the coupling portion 1420 includes tapered projections 1422 which extend away from an external surface of the terminal pin 1410. Alternatively, the tapered projections 1422 can have other shapes such as a rounded projection. The tapered projections 1422 include at least one mating surface 1424, for coupling with a portion of the sleeve 1440, as discussed further below. Although a plurality of projections 1422 are discussed, a single projection can also be used.

The sleeve 1440 extends from a first end 1442 to a second end 1444, and includes a first set of coupling features 1445 for coupling with the outer terminal ring 1470. In addition, the sleeve 1440 includes a second set of coupling features 1450 for coupling with the terminal pin 1410.

The second set of coupling features 1450, in one embodiment, comprise cutouts 1452 formed in cantilever panels 1453. The cantilever panels 1453 are adapted to deflect when an internal or external force is placed thereon. The cutouts 1452 correspond in size and shape and are adapted to receive therein the tapered projections 1422 of the terminal pin 1410. In another embodiment, the number of cutouts 1452 correspond to the number of tapered projections 1422. The cutouts 1452 include mating surfaces 1454 which are adjacent to the mating surfaces 1424 of the terminal pin 1410 when the sleeve 1440 is assembled with the terminal pin 1410.

As mentioned above, the sleeve 1440 also includes a first set of coupling features 1445 for coupling the sleeve 1440 with the outer terminal ring 1470. The first set of coupling features 1445, which in one embodiment are disposed at the first end 1442 of the sleeve 1440, comprise cantilever hooks 1446 which include tapered portions 1447 and also mating surfaces 1448. The cantilever hooks 1446 are adapted to deflect when an external or internal force is placed thereon. The first set of coupling features 1445 are adapted to be received by the outer terminal ring 1470. In another embodiment, a positive stop 1456 is formed integral with the sleeve 1440 and is disposed adjacent to the first set of coupling features 1445.

The outer terminal ring extends from a first end 1474 to a second end 1476 and includes an inner surface 1472 which receives the sleeve 1440 therein. The outer terminal ring 1470 further includes snap-fit coupling features 1478. In one embodiment, the snap-fit coupling features 1478 comprise a tapered surface 1484 formed proximate to the second end 1476 of the outer terminal ring 1470. The tapered surface 1484 is formed near a ridge 1480, which engages with the first set of coupling features 1445 of the sleeve 1440. In another embodiment, the coupling features 1478 include a mating surface 1482 which is placed adjacent to the mating surfaces 1448 of the sleeve 1440.

To form the snap-fit assembly 1400, the terminal pin 1410 is assembled with the sleeve 1440 and the sleeve 1440 is assembled with the outer terminal ring 1470. However, the sleeve 1440 can be assembled with the outer terminal ring 1470 prior to assembly of the terminal pin 1410 with the sleeve 1440. To assemble the terminal pin 1410 with the sleeve 1440, the first end 1412 of the terminal pin 1410 is inserted into and through the second end 1444 of the sleeve 1440. The first end 1412 is inserted until the tapered projections 1422 are seated within the second set of coupling features 1450 of the sleeve 1440. As the terminal pin 1410 is inserted through the sleeve 1440, the tapered projections 1422 deflect the cantilever panels 1453 outward of the sleeve 1440. The cantilever panels 1453 are deflected until the tapered projections 1422 are seated within the cutouts 1452 of the sleeve, and the mating surfaces 1454 of the cutouts 1452 abut the mating surfaces 1424 of the terminal pin 1410.

To assemble the sleeve 1440 to the outer terminal ring 1470, the first end 1442 of the sleeve 1440 is inserted into the second end 1476 of the outer terminal ring 1470. As the sleeve 1440 is inserted into the outer terminal ring 1470, the first set of coupling features 1445 are deflected as they approach the tapered surface 1484 of the outer terminal ring. The sleeve 144Q is further inserted until the mating surfaces 1448 are seated against the mating surface 1482 of the outer terminal ring. The cantilever hooks 1446 are retained by the annular ridge 1480 of the outer terminal ring 1470.

The terminal pin 1410 and the outer terminal ring 1470 are each formed of a conductive material. The sleeve 1440 is formed from a nonconductive material, and acts as an insulator between the terminal pin 1410 and the outer terminal ring 1470, in one embodiment. The sleeve 1440 can be formed from various high-performance engineering plastics, unreinforced and reinforced materials including, but not limited to polysulfone, polyimide, polyamide, polyacetal, polyketone, polyester, polycarbonate, polyolefin, or liquid crystal polymers.

Figure 14:
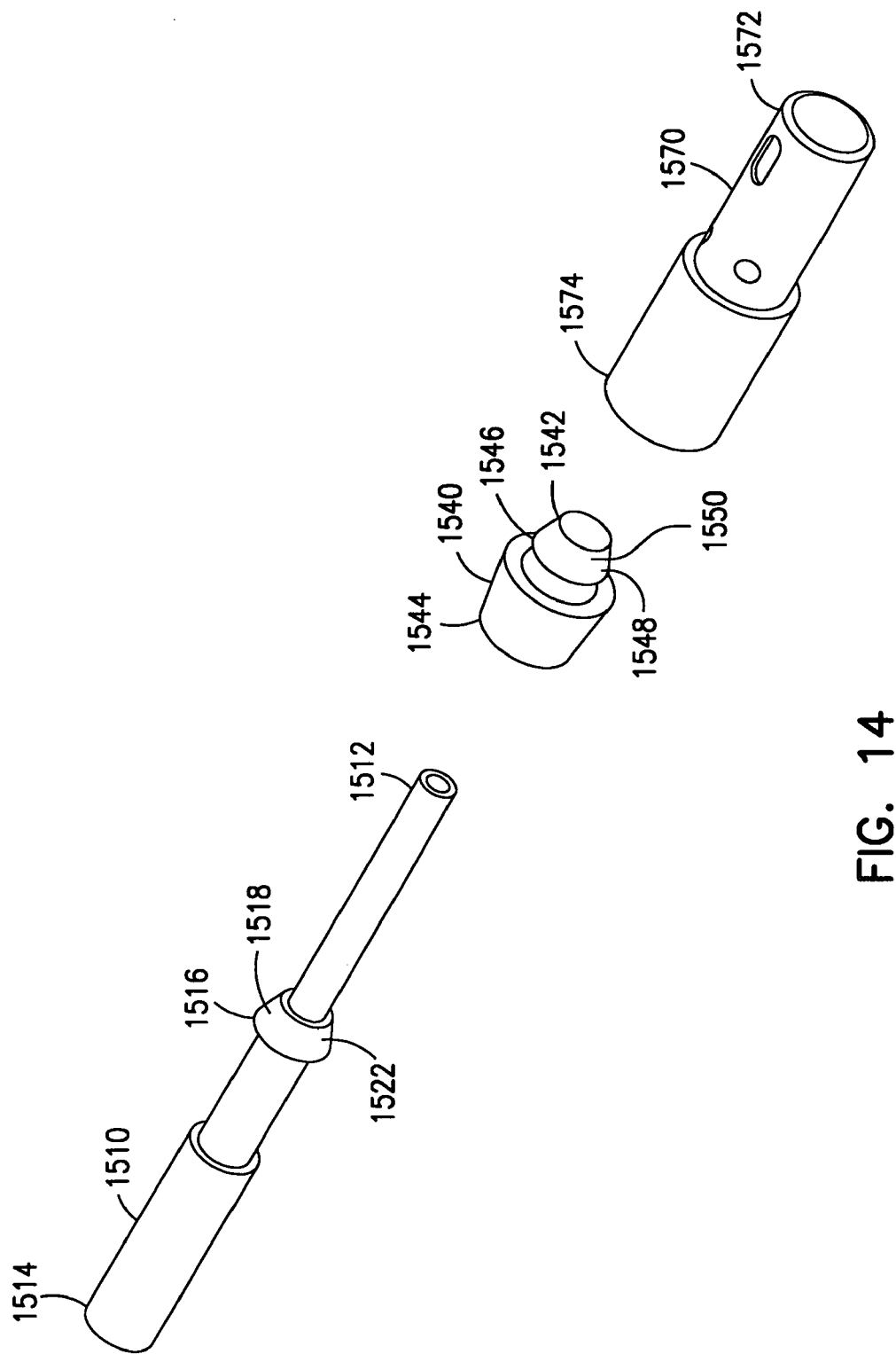
FIG. 14 is an exploded perspective view of an assembly constructed in accordance with one embodiment.
Figure 15:
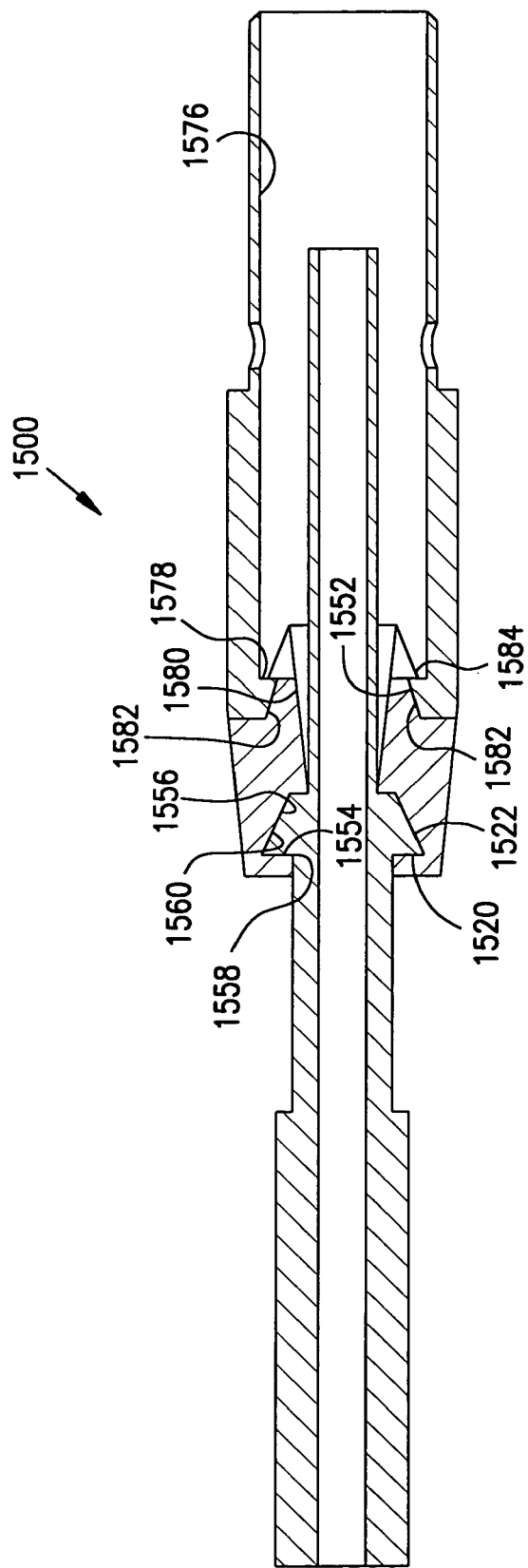
FIG. 15 is an unexploded cross-sectional view of the assembly shown in FIG. 14 constructed in accordance with one embodiment.
Figure 19:
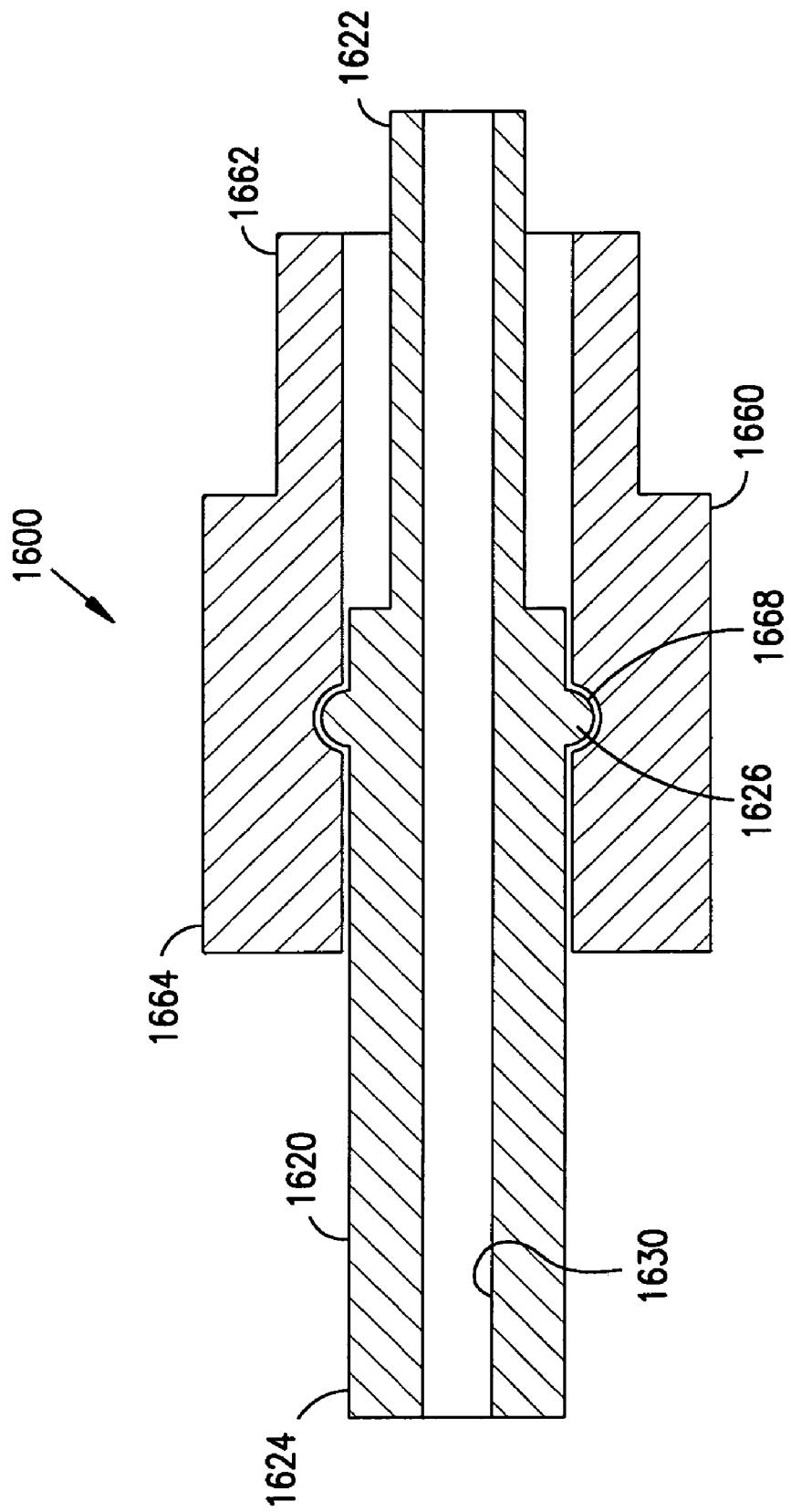
FIG. 19 is an unexploded cross-sectional view of an assembly constructed in accordance with one embodiment.

FIGS. 14 and 15 illustrate another embodiment of a snap-fit assembly 1500, which includes generally a terminal pin 1510, a sleeve 1540, and an outer terminal ring 1570. The terminal pin 1510 extends from a first end 1512 to a second end 1514, and includes at least one coupling portion 1516. In one embodiment, the coupling portion 1516 is disposed between the first end 1512 and the second end 1514 of the terminal pin 1510. In another embodiment, the coupling portion 1516 comprises an annular projection 1518 which extends from an external surface of the terminal pin 1510. The annular projection 1518, in another embodiment, includes a tapered surface 1522 and also a mating surface 1520. The coupling portion 1516 allows for the terminal pin 1510 to be coupled with the sleeve 1540 using a snap-fit connection.

The sleeve 1540 is adapted to couple with both the terminal pin 1510 and also the outer terminal ring 1570, and extends generally from a first end 1542 to a second end 1544. Proximate to the first end 1542, is a first coupling feature 1546, which allows for the sleeve 1540 to be coupled with the outer terminal ring 1570. In one embodiment, the first coupling feature 1546 comprises an annular projection 1548 including a tapered surface 1550 and a mating surface 1552. The sleeve 1540 also includes a second coupling feature 1554 which, in one embodiment, comprises an annular recess 1556. In yet another embodiment, the annular recess 1556 includes a ridge 1558 and also a mating surface 1560, which is adapted to couple with the annular projection 1518.

The outer terminal ring 1570 is adapted to couple with the sleeve 1540, and generally extends from a first end 1572 to a second end 1574. The outer terminal ring 1570 is defined in part by an inner surface 1576 which is adapted to receive a portion of the sleeve 1540 therein. The outer terminal ring 1570 further includes at least one snap-fit coupling feature 1578 which allows for the sleeve 1540 to be coupled with the outer terminal ring 1570. In one embodiment, the coupling feature 1578 includes a tapered ingress 1582 which extends to a ridge 1580. The ridge 1580 includes a mating surface 1584, and is adapted to retain the first coupling feature 1546 of the sleeve 1540. In one embodiment, the tapered ingress 1582 and/or the ridge 1580 are formed on the inner surface 1576 of the outer terminal ring 1570. In another embodiment, the tapered ingress 1582 is formed annularly of the inner surface 1576.

To assemble the snap-fit assembly 1500, the terminal pin 1510 is coupled with the sleeve 1540, and the sleeve 1540 is coupled with the outer terminal ring 1570. It should be noted however, that the sleeve 1540 can also be first coupled with the outer terminal ring 1570 and then the terminal pin 1510 is coupled with the sleeve 1540. To couple the terminal pin 1510 to the sleeve 1540, the first end 1512 of the terminal pin 1510 is inserted into the second end 1544 of the sleeve 1540. The terminal pin 1510 is inserted until the coupling portion 1516 is seated within the second coupling feature 1554, of the sleeve. Once the annular projection 1518 is seated within the annular recess 1556, the mating surface 1520 abuts the mating surface 1560 of the sleeve 1540.

To assemble the sleeve 1540 to the outer terminal ring 1570, the first end 1542 of the sleeve 1540 is inserted into the second end 1574 of the outer terminal ring 1570. As the sleeve 1540 is inserted into the outer terminal ring 1570, the tapered surface 1550 deflects the tapered ingress 1582 of the outer terminal ring 1570. The sleeve 1540 is further inserted into the outer terminal ring 1570, until the mating surface 1552 of the first coupling feature 1546 abuts the mating surface 1584 of the outer terminal ring 1570.

The terminal pin 1510 and the outer terminal ring 1570 are each formed of a conductive material. The sleeve 1540 is formed from a nonconductive material, and acts as an insulator between the terminal pin 1510 and the outer terminal ring 1570, in one embodiment. The materials suitable for the sleeve 1540 are similar to those described for the sleeve discussed above in earlier embodiments The snap-fit assembly 1500 provides several advantages in that the assembly allows for rotational movement, yet prevents axial movement of the terminal pin 1510 relative to the sleeve 1540, and the sleeve 1540 relative to the outer terminal ring 1570. The rotational movement which is allowed by the snap-fit assembly 1500 is advantageous since the snap-fit assembly 1500 can be used in combination with retractable lead designs, or leads which otherwise require rotational movement and yet simultaneously prevent axial movement.

FIGS. 16, 17, and 18 illustrate another embodiment of a snap fit assembly 1600, which includes generally a terminal pin 1620 and an outer terminal ring 1660. The terminal pin 1620 and the outer terminal ring 1660 are adapted to couple together at a snap-fit coupling, as further described below.

The terminal pin 1620 extends from a first end 1622 to a second end 1624, and includes a snap-fit coupling portion 1626. In one embodiment, the coupling portion 1626 is disposed between the first end 1622 and the second end 1624. It should be noted that the coupling portion 1626 can be disposed on an external surface or an internal surface of the terminal pin 1620. In another embodiment, the coupling portion 1626 comprises an annular projection 1640, as shown in FIG. 17. The annular projection 1640 has a semi-circular cross-section, as shown in FIG. 16. In another embodiment, the coupling portion 1626 comprises at least one projection 1642, which does not extend completely around the outer surface of the terminal pin 1620, as illustrated in FIG. 17. A plurality of projections 1643 can also be provided, as shown in FIG. 18. In another embodiment, the plurality of projections 1643 are spaced 90 degrees apart from one another.

Disposed through the terminal pin 1620 a bore 1630, where the bore 1630 extends from the first end 1622 to the second end 1624 of the terminal pin 1620. The bore 1630 allows for instruments, such as catheters, stylets, or guidewires, to be inserted through the terminal pin 1620 and through the lead 1110 (FIG. 7B).

In yet another embodiment, an insulator is disposed between the terminal pin 1620 and the outer terminal ring 1660. The insulator can be a shim, a tube, a wedge, or a coating placed between the terminal pin 1620 and the outer terminal ring 1660. In one embodiment, a dielectric coating 1628 is disposed on the interfacing surfaces between the terminal pin 1620 and the outer terminal ring 1660. In another embodiment, the coating is disposed over the coupling portion 1626. The dielectric coating 1628 provides insulation for the coupling portion 1626 and/or the surface of the terminal pin 1620. Various insulating materials are appropriate for use as the coating 1628 such as: tungsten carbide, aluminum oxide, chromium oxide, zirconium oxide, magnesium zirconate, acrylic, epoxy, parylene, polyurethane, silicone, teflon, or molybdenum disulfide. Other materials which are also dielectric, biocompatible, wear resistant, and has a low coefficient of friction would also be appropriate. The coupling portion 1626 of the terminal pin 1620 is adapted to snap-fit with a coupling portion of the outer terminal ring 1660.

The outer terminal ring 1660 extends from a first end 1662 to a second end 1664, and includes a snap-fit coupling portion 1668. The snap-fit coupling portion 1668, in one embodiment, is disposed on an intermediate portion 1665 of the outer terminal ring 1660. In another embodiment, the coupling portion 1668 is disposed on an inner surface 1666 of the outer terminal ring 1660. The coupling portion 1668 comprises an annular recess 1670 which is sized and positioned to receive the snap-fit coupling portion 1626 of the terminal pin 1620 therein.

To assemble the snap-fit assembly 1600, the terminal pin 1620 is coupled with the outer terminal ring 1660. To assembly the terminal pin 1620 to the outer terminal ring 1660, the first end 1622 of the terminal pin 1620 is inserted into the second end 1664 of the outer terminal ring 1660. The terminal pin 1620 is inserted until the annular projection 1640 is seated within the annular recess 1670 of the outer terminal ring 1660. Once the projection 1640 is seated within the recess 1670, further axial movement is prevented. However, rotational movement of the terminal pin 1620 relative to the outer terminal ring 1660 is permitted.

Several embodiments are described above which relate to snap fit features for the terminal pin and the outer terminal ring and, optionally, the sleeve. It should be noted that the features shown in the drawings can be exchanged between embodiments shown in the various drawings. In addition, the coupling features have been described on an external surface of one component which mates with an internal surface of another component. However, the coupling features can be moved from internal to external surfaces and vice versa to accommodate the snap-fit features and/or the press-fit features. Furthermore, the lead design is not limited to the particular embodiments shown or described above, and can be applied to various medical devices. It should be further noted that embodiments discussed for the distal end of the lead can be combined with any of the embodiments for the proximal end of the lead.

The lead assembly described above provides several advantages, for example, the ease of manufacturability is increased in that through-put times are reduced. The individual components can be snapped together, as opposed to waiting for messy bonding or long cure times. Bonding blocks, used for the bonding process, would be eliminated, which are expensive and difficult and costly to clean. A consistent and increased strength of coupling would be achieved using the snap fit design since bonding is variable based on the operator. Yet another advantage is that the geometry of the snap fit connector provides an insulation with a known thickness, which allows for a repeatable dielectric strength. Furthermore, the active fixation element of the lead does not require the use of a stylet, since the terminal pin is used to extend and retract the active fixation element. In addition, the movement assembly allows for the lead to withstand high shearing forces applied between the terminal pin and the outer terminal components such as the ring.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead for a medical device, the lead comprising:
a lead body extending from a distal end portion to a proximal end portion;
at least one conductor disposed within the lead body and extending from the proximal end portion;
an electrically conductive terminal pin disposed at the proximal end portion of the lead body, the electrically conductive terminal pin having at least recess;
an insulative sleeve coupled with the electrically conductive terminal pin with a snap-fit connection; and
the snap-fit connection includes a rotatable snap-fitted connection that allows rotation of the terminal pin relative to the sleeve after the sleeve is snap-fittedly coupled with the terminal pin, and the terminal pin is rotatable relative to the sleeve.

2. The lead as recited in claim 1, wherein the snap-fit connection comprises a rotatable snap-fitted connection that allows rotation of the terminal pin relative to the sleeve after the sleeve is snap-fittedly coupled with the terminal pin.

3. The lead as recited in claim 1, wherein the snap-fit connection comprises an annular flange received in an annular recess.

4. The lead as recited in claim 1, further comprising an outer terminal ring coupled with the insulative sleeve.

5. The lead as recited in claim 4, wherein the sleeve further comprises a positive stop for the outer terminal ring.

6. The lead as recited in claim 4, wherein the sleeve comprises a snap-fit coupling disposed proximate to the outer terminal ring.

7. The lead as recited in claim 1, wherein at least the sleeve is coated with a non-conductive material.

8. The lead as recited in claim 7, wherein the non-conductive coating is disposed on the outer surface of the terminal pin.

9. The lead as recited in claim 8, wherein non-conductive material is disposed between the outer terminal ring and the terminal pin.

10. The lead as recited in claim 1, wherein the sleeve forms an insulator between the outer terminal ring and the terminal pin.

11. The lead as recited in claim 1, wherein the sleeve is formed of polyetheretherketone.

12. The lead as recited in claim 1, further comprising
the sleeve including a projection mated with a recess within the terminal pin, and the projection comprises an annular projection disposed about a circumference of the sleeve, and the recess comprises an annular recess disposed about a circumference of the terminal pin; and
the terminal pin is rotatable relative to the lead body and the sleeve, the terminal pin coupled with a fixation member, rotation of the terminal pin rotates the fixation member.

13. The lead as recited in claim 1, further comprising a male component on the terminal pin and a female component on the sleeve.

14. The lead as recited in claim 13, wherein the male component comprises an annular projection and the female component comprises an annular recess.

15. The lead as recited in claim 12, further comprising an active fixation mechanism disposed proximate to the distal end of the lead body, the active fixation mechanism including a movement assembly coupled therewith; the movement assembly configured to extend and retract the active fixation mechanism, the movement assembly including:
an internally threaded portion; and an externally threaded collar engaged with the internally threaded portion.

16. The lead as recited in claim 1, further comprising
an active fixation mechanism disposed proximate to the distal end of the lead body, the active fixation mechanism including a movement assembly coupled therewith; the movement assembly configured to extend and retract the active fixation mechanism, the movement assembly including:
a housing having an internally threaded portion; and an externally threaded collar engaged with the internally threaded portion.

17. The lead as recited in claim 16, wherein the movement assembly further comprises an internally threaded insert disposed within the lead body, where the threaded collar is engaged with the threaded insert.

18. The lead as recited in claim 16, wherein the externally threaded collar comprises an electrode base.

19. The lead as recited in claim 16, further comprising a fixation helix coupled with an externally threaded electrode base, and an outer threaded shell having internal threads, the outer threaded shell disposed within the distal end of the lead body, the outer threaded shell threadingly coupled with the electrode base.

20. The lead as recited in claim 19, wherein the conductor is mechanically and electrically coupled with the terminal pin and the fixation helix such that as the terminal pin is rotated, the fixation helix is rotated.

* * * * *